(12) United States Patent
Gibson et al.

(10) Patent No.: US 6,441,000 B1
(45) Date of Patent: Aug. 27, 2002

(54) COMPOUNDS USEFUL IN THERAPY

(75) Inventors: Stephen Paul Gibson; Ivan Tommasini; Kimberley Verrier; Lee Roberts, all of Sandwich (GB); Brian Scott Bronk, Gales Ferry, CT (US); Richard Edward Armer, Newhouse (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/573,300

(22) Filed: May 18, 2000

(30) Foreign Application Priority Data

May 28, 1999 (GB) .............................. 9912413

(51) Int. Cl.7 ..................... C07D 401/04; A61K 31/445
(52) U.S. Cl. ....................................... 514/322; 546/199
(58) Field of Search ........................ 514/322; 546/199

(56) References Cited

U.S. PATENT DOCUMENTS

| 4,081,450 A | 3/1978 | Zimmerman ................ 546/185 |
| 4,191,771 A | 3/1980 | Zimmerman ................ 514/317 |
| 4,737,505 A | 4/1988 | Guillaume et al. ......... 514/323 |
| 5,136,040 A | 8/1992 | Werner ....................... 546/218 |
| 5,498,718 A | 3/1996 | Werner ....................... 546/348 |

FOREIGN PATENT DOCUMENTS

| DE | 4341403 | 6/1995 |
| EP | 0013078 | 7/1980 |
| EP | 0136863 | 4/1985 |
| EP | 0506468 A1 | 3/1992 |
| EP | 0506468 B1 | 3/1992 |
| EP | 0287339 | 8/1994 |
| EP | 0657428 | 6/1995 |
| EP | 0506478 | 9/1997 |
| EP | 0938898 | 9/1999 |
| GB | 2038812 | 7/1980 |
| WO | 9515327 | 6/1995 |
| WO | 9603400 | 2/1996 |
| WO | 9850358 | 11/1998 |
| WO | 9959971 | 11/1999 |
| WO | 9967237 | 12/1999 |
| WO | 0039089 | 7/2000 |

OTHER PUBLICATIONS

Charles H. Mitch, et al.; 3,4–Dimethyl–4–(3–hydroxyphenyl)piperidines: Opioid Antagonists with Potent Anorectant Activity; J. Med. Chem. (1993) 36, 2842–2850.

Dennis M. Zimmerman, et al.; Structure–Activity Relationships of trans–3,4–Dimethyl–4–(3–hydroxyphenyl)piperidine Antagonists for $\mu$– and $\kappa$–Opioid Receptors; J. Med. Chem (1993) 36, 2833–2841.

Patent Abstract of Japan, vol. 13, No. 179 (C–590), 1988.

*Primary Examiner*—Zinna Northington Davis
(74) *Attorney, Agent, or Firm*—Peter C. Richardson; Paul H. Ginsburg; Kristina L. Konstas

(57) ABSTRACT

There is provided a compound of formula I,

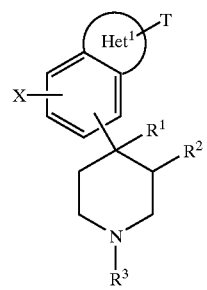

wherein $Het^1$, T, X, $R^1$, $R^2$ and $R^3$ have meanings given in the description, which are useful in the prophylaxis and in the treatment of diseases mediated by opiate receptors, such as pruritus.

15 Claims, No Drawings

COMPOUNDS USEFUL IN THERAPY

This application claims priority under 35 U.S.C. 119 of GB 9912413.3, filed May 28, 1999.

FIELD OF THE INVENTION

This invention relates to pharmaceutically useful compounds, in particular compounds that bind to opiate receptors (e.g. mu, kappa and delta opioid receptors).

BACKGROUND OF THE INVENTION

Compounds that bind to such receptors are likely to be useful in the treatment of diseases mediated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction, sexual dysfunction, shock, stroke, spinal damage and head trauma.

There is a particular need for an improved treatment of itching. Itching, or pruritus, is a common dermatological symptom that can give rise to considerable distress in both humans and animals. Pruritus is often associated with inflammatory skin diseases which may be caused by hypersensitivity reactions, including reactions to insect bites, such as flea bites, and to environmental allergens, such as house dust mite or pollen; by bacterial and fungal infections of the skin; or by ectoparasite infections.

Existing treatments that have been employed in the treatment of pruritus include the use of corticosteroids and antihistamines. However, both of these treatments are known to have undesirable side effects. Other therapies that have been employed include the use of essential fatty acid dietary supplements, though these have the disadvantages of being slow to act, and of offering only limited efficacy against allergic dermatitis. A variety of emollients such as soft paraffin, glycerine and lanolin are also employed, but with limited success.

Thus, there is a continuing need for alternative and/or improved treatments of pruritus.

Certain 4-arylpiperidine-based compounds are disclosed in inter alia European patent applications EP 287339, EP 506468, EP 506478 and *J. Med. Chem.* 1993, 36, 2833–2850 as opioid antagonists. In addition, International Patent Application WO 95/15327 discloses azabicycloalkane derivatives useful as neuroleptic agents.

SUMMARY OF THE INVENTION

According to the invention there is provided compounds of formula I:

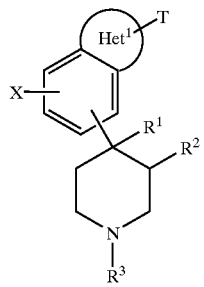

wherein $Het^1$ represents a 5-, 6- or 7-membered heterocyclic ring containing at least one nitrogen atom, and optionally one or more heteroatoms selected from oxygen or sulfur, and which heterocyclic ring is fully saturated, partially unsaturated or aromatic in character;

T represents one or more optional substituents selected from H, halo, OH, =O, $C_{1-6}$ alkyl, $C_{1-6}$ alkoxy, $C_{3-6}$ cycloalkyl (which latter three groups are optionally substituted by one or more halo atoms), aryl($C_{1-6}$)alkyl (the aryl part of which is optionally substituted by one or more substituents selected from halo, $C_{1-4}$ alkyl and $C_{1-4}$ alkoxy (which latter two groups are optionally substituted by one or more halo atoms)), —N($R^{4a}$)($R^5$), —N($R^{4b}$)S(O)$_m R^6$, —N($R^{4c}$)C(O)$R^{7a}$ and —N($R^{4d}$)C(O)O$R^{7b}$, provided that when $Het^1$ contains less than three C-atoms (i.e. where the only two C-atoms are those provided by the fused benzene ring) and at least one heteroatom selected from oxygen and sulfur, then T does not represent halo or $C_{1-6}$ alkoxy (which latter group is optionally substituted by one or more halo atoms);

$R^{4a}$ to $R^{4d}$ and $R^5$ independently represent H, $C_{1-6}$ alkyl (which latter group is optionally substituted by one or more halo atoms), or $R^{4a}$ and $R^5$, together with the nitrogen atom to which they are attached, form a 4- to 6-membered heterocyclic ring (which ring is optionally substituted by one or more substituents selected from $C_{1-4}$ alkyl, $C_{1-4}$ alkoxy, OH, =O, nitro, amino or halo);

$R^6$ represents $C_{1-6}$ alkyl or aryl, which two groups are optionally substituted by one or more substituents selected from halo, $C_{1-4}$ alkyl or nitro;

$R^{7a}$ and $R^{7b}$ independently represent $C_{1-6}$ alkyl, $C_{1-6}$ alkoxy, $C_{3-6}$ cycloalkyl, aryl (which four groups are optionally substituted by one or more substituents selected from halo, $C_{1-4}$ alkyl or nitro), or $R^{7a}$ represents H;

m is 0, 1 or 2;

$R^1$ and $R^2$ are each independently H or $C_{1-4}$ alkyl;

$R^3$ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —N($R^{8a}$)($R^{8b}$)), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{8c}$, S(O)$_n R^{8d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, N($R^{9a}$)S(O)$_2 R^{10}$, $Het^2$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or —W—$A^1$—N($R^{9b}$)($R^{9c}$);

n is 0, 1 or 2;

W represents a single bond, C(O) or S(O)$_p$;

$A^1$ represents a single bond or $C_{1-10}$ alkylene; provided that when both W and $A^1$ represent single bonds, then the group —N($R^{9b}$)($R^{9c}$) is not directly attached to an unsaturated carbon atom;

p is 0, 1 or 2;

$R^{8a}$ to $R^{8d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^3$;

provided that $R^{8d}$ does not represent H when n represents 1 or 2;

$R^{9a}$ to $R^{9c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^4$, or $R^{9b}$ and $R^{9c}$ together represent unbranched $C_{2-6}$ alkylene which alkylene group is optionally interrupted by O, S and/or an N($R^{11}$) group and is optionally substituted by one or more $C_{1-4}$ alkyl groups;

$R^{10}$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

$R^{11}$ represents H, $C_{1-6}$ alkyl, $C_{3-8}$ cycloalkyl, $A^2$—($C_{3-8}$ cycloalkyl) or $A^2$-aryl;

$A^2$ represents $C_{1-6}$ alkylene;

$Het^2$, $Het^3$ and $Het^4$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

X represents one or two optional substituents on the benzene ring, which substituents are selected from halo, $C_{1-4}$ alkyl, $C_{1-4}$ alkoxy (which latter two groups are optionally substituted by one or more halo atoms);

or pharmaceutically, or veterinarily, acceptable derivatives thereof;

which compounds are referred to together hereinafter as "the compounds of the invention."

DETAILED DESCRIPTION OF THE INVENTION

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_{1-4}$ alkyl, $C_{1-4}$ alkoxy $C_{1-4}$ alkoxy carbonyl and $C_{1-5}$ alkanoyl (which latter four groups are optionally substituted by one or more halo atoms).

The heterocyclic rings that $Het^2$, $Het^3$ and $Het^4$ represent and that N($R^{4a}$)($R^5$) may represent, may be fully saturated, partially unsaturated and/or wholly or partially aromatic in character. Specific rings that may be mentioned include: for $Het^2$, dioxane, dioxolane, morpholine, piperidine, perhydroazepine, tetrahydrofuran, tetrahydropyran or tetrazole.

For the avoidance of doubt, when heterocyclic groups (i.e. $Het^2$, $Het^3$, $Het^4$ and some definitions of N($R^{4a}$)($R^5$)) are at least part-saturated, possible points of substitution include the atom (e.g. the carbon atom) at the point of attachment of the heterocyclic group to the rest of the molecule. Het ($Het^2$, $Het^3$ and $Het^4$) groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All heterocyclic groups (i.e. $Het^1$, $Het^2$, $Het^3$, $Het^4$ and some definitions of N($R^4$)($R^5$)) may also be in N- or S-oxidized forms.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succiric, tartaric, cinnamic, ascorbic and related acids; base addition salts; salts formed with bases, for example, the sodium, potassium and $C_{1-4}$ alkyl ammonium salts.

The compounds of the invention may also be in the form of quaternary ammonium salts, e.g. at the piperidine moiety, which salts may be formed by reaction with a variety of alkylating agents, such as an alkyl halide or an ester of sulfuric, or an aromatic sulfonic, acid.

The compounds of the invention may exhibit tautomerism. All tautomeric forms of the compounds of formula I are included within the scope of the invention.

The compounds of the invention contain one or more asymmetric centres and thus they can exist as enantiomers and diastereomers. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers.

Also included within the scope of the invention are radiolabelled derivatives of compounds of formula I which are suitable for biological studies.

Preferred compounds of the invention include those wherein:

$Het^1$ is fused at the 3,4-position on the benzene ring relative to the piperidine ring;

$R^1$ represents $C_{1-2}$ alkyl;

$R^2$ represents H or $C_{1-2}$ alkyl;

$R^3$ represents saturated $C_{1-10}$ (e.g. $C_{1-8}$) alkyl, optionally interrupted by oxygen and/or optionally substituted by one or more substituents selected from $OR^{8c}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{9a})S(O)_2R^{10}$, $Het^2$, phenyl (which latter group is optionally substituted by one or more substituents selected from OH, $C_{1-4}$ alkyl, $C_{1-4}$ alkoxy, $C_{2-5}$ alkanoyl, halo, nitro, amino, CN, $CH_2CN$, $CONH_2$ and $CF_3$), and/or —W—$A^1$—$N(R^{9b})(R^{9c})$; $R^{8c}$ represents H, $C_{1-6}$ alkyl, $C_{3-8}$ cycloalkyl, phenyl or $C_{1-4}$ alkylphenyl (which latter two groups are optionally substituted by one or more substituents selected from OH, $C_{1-4}$ alkyl, $C_{1-4}$ alkoxy, $C_{2-5}$ alkanoyl, halo, nitro, amino, CN, $CH_2CN$, $CONH_2$ and $CF_3$);

$R^{9a}$ to $R^{9c}$ each independently represent H, $C_{1-4}$ alkyl, $C_{1-2}$ alkylphenyl or aryl (which latter two groups are optionally substituted by or one or more substituents selected from $C_{1-2}$ alkyl, $C_{1-2}$ alkoxy, OH or halo);

$R^{10}$ represents $C_{1-4}$ alkyl or aryl, which two groups are optionally substituted by or one or more substituents selected from $C_{1-2}$ alkyl, $C_{1-2}$ alkoxy, nitro or halo;

W represents C(O) or $S(O)_2$;

$A^1$ represents a single bond or $C_{1-4}$ alkylene;

T represents H, OH, $C_{1-6}$ alkyl (optionally substituted with one or more halo atoms), $C_{1-4}$ alkoxy, $C_{4-6}$ cycloalkyl, aryl($C_{1-3}$)alkyl, —$NH(R^5)$ or —$N(H)S(O)_2R^6$;

$R^5$ represents H or $C_{1-2}$ alkyl;

$R^6$ represents $C_{1-2}$ alkyl.

More preferred compounds of the invention include those wherein:

$Het^1$ represents a 5- or 6-membered heterocyclic ring, optionally containing an NH group;

$R^1$ represents methyl;

$R^2$ represents H or methyl;

$R^3$ represents saturated $C_{1-7}$ alkyl, optionally substituted by one or more substituents selected from $OR^{8c}$, CN, halo and phenyl (which latter group is optionally substituted by one or more $C_{1-4}$ alkyl groups);

$R^{8c}$ represents H, $C_{1-4}$ alkyl, phenyl or $C_{1-4}$ alkylphenyl (which latter two groups are optionally substituted by one or more $C_{1-4}$ alkyl groups);

T represents H, $NH_2$, $C_{4-6}$ cycloalkyl or $C_{1-6}$ alkyl (which latter group is optionally substituted by one or more halo atoms);

X represents halo, particularly fluoro.

Still further preferred compounds of the invention include those wherein: $Het^1$, together with the benzene ring to which it is fused, represents an aromatic heterocycle, particularly a benzimidazole, benzotriazole, benzoxadiazole, benzoxazole, benzothiazole, cinnoline, indole, isoquinoline, phthalazine, quinazoline, quinoline or quinoxaline group;

T represents H, $CH_3$, $CHF_2$, $CF_3$, ethyl, isopropyl, $C_{4-5}$ cycloalkyl or $NH_2$;

$R^1$ and $R^2$ both represent methyl groups in the mutually trans configuration;

$R^3$ represents saturated $C_{1-7}$ alkyl, optionally substituted by one or more substituents selected from $OR^{8c}$ and phenyl, (which latter group is optionally substituted by one or more $C_{1-2}$ alkyl groups);

$R^{8c}$ represents $C_{2-4}$ alkyl, phenyl or $C_{1-2}$ alkylphenyl.

Particularly preferred compounds of the invention include those wherein:

$Het^1$, together with the benzene ring to which it is fused, represents a benzirnidazole group;

T represents H, $CHF_2$ or $CF_3$.

Preferred compounds of the invention include the compounds of the Examples described hereinafter.

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I wherein $Het^1$ represents the 5-membered ring of a benzimidazole, optionally substituted in the 2-position by $C_{1-6}$ alkyl, $C_{1-6}$ alkoxy, $C_{3-6}$ cycloalkyl (which three groups are optionally substituted by one or more halo atoms) or aryl($C_{1-6}$)alkyl (the aryl part of which is optionally substituted by one or more substituents selected from halo, $C_{1-6}$ alkyl and $C_{1-6}$ alkoxy, which latter two groups are optionally substituted by one or more halo atoms), may be prepared by reaction of a corresponding compound of formula II,

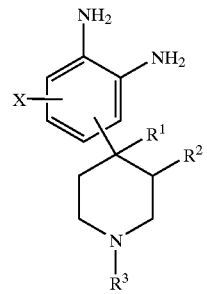

II wherein $R^1$, $R^2$, $R^3$ and X are as hereinbefore defined, with a compound of formula III,

III, wherein $T^a$ represents H, $C_{1-6}$ alkyl $C_{1-6}$ alkoxy, $C_{3-6}$ cycloalkyl (which latter three groups are optionally substituted by one or more halo atoms) or aryl($C_{1-6}$)alkyl (the aryl group of which is optionally substituted by one or more substituents selected from halo, $C_{1-6}$ alkyl and $C_{1-6}$ alkoxy, which latter two groups are optionally substituted by one or more halo atoms) and $R^{12}$ represents $C_{1-2}$ alkyl, for example at between room and reflux temperature in the presence of a suitable solvent and/or acidic catalyst (e.g. acetic acid).

Compounds of formula II may be prepared by reduction of a corresponding nitroaniline of formula IV,

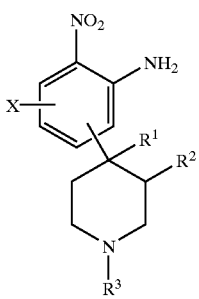

IV

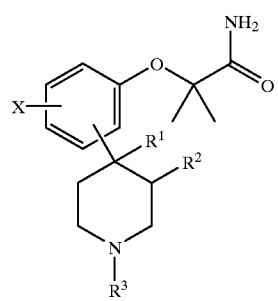

VII wherein $R^1$, $R^2$, $R^3$ and X are as hereinbefore defined, for example by hydrogenation under standard catalytic conditions, or in the presence of a suitable reducing agent (e.g. finely divided metallic iron combined with calcium chloride) and an appropriate solvent (e.g. water or a water/alcohol mixture).

Compounds of formula IV may be prepared by nitration of a corresponding aniline of formula V,

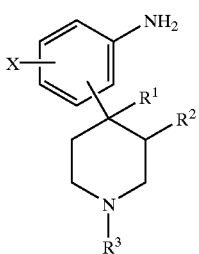

V wherein $R^1$, $R^2$, $R^3$ and X are as hereinbefore defined, under conditions known to those in the art, for example by reaction with a suitable nitronium salt (e.g. nitronium tetrafluoroborate) in the presence of an appropriate solvent (e.g. acetonitrile).

Compounds of formula V may be prepared by hydrolysis of a corresponding compound of formula VI,

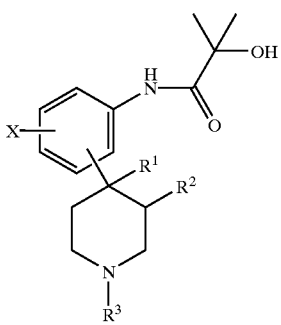

VI wherein $R^1$, $R^2$, $R^3$ and X are as hereinbefore defined, under conditions known to those skilled in the art, for example by reaction at between room and reflux temperature with a suitable strong acid (e.g. HCl) and (optionally) an appropriate co-solvent (e.g. dioxan).

Compounds of formula VI may be prepared by rearrangement of a corresponding compound of formula VII, wherein $R^1$, $R^2$, $R^3$ and X are as hereinbefore defined, for example at between 25 and 200° C. in the presence of a suitable strong base (e.g. sodium hydride) and an appropriate solvent (e.g. 1-methyl-2-pyrrolidinone or N,N-dimethylformamide).

Compounds of formula VII may be prepared by reaction of a corresponding compound of formula VIII,

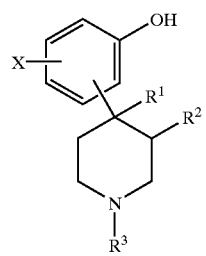

VIII wherein $R^1$, $R^2$, $R^3$ and X are as hereinbefore defined, with a compound of formula IX, $$L^1-C(CH_3)_2C(O)NH_2 \qquad \text{IX}$$

wherein $L^1$ is a suitable leaving group (e.g. halo, arene sulfonate, alkane sulfonate or perfluoroalkane sulfonate), for example at between room and reflux temperature in the presence of a suitable base (e.g. caesium carbonate in combination with sodium hydride) and an appropriate solvent (e.g. dioxan).

Compounds of formula VIII may be prepared by reaction of a corresponding compound of formula X,

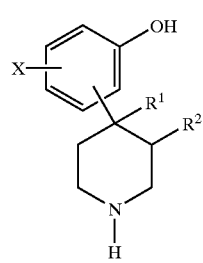

X wherein $R^1$, $R^2$ and X are as hereinbefore defined, with a compound of formula XI, $$R^3L^1 \qquad \text{XI}$$

wherein $R^3$ and $L^1$ are as hereinbefore defined, for example under conditions known to those skilled in the art, which include, for example, alkylation at between room temperature and reflux temperature in the presence of a reaction-inert organic solvent (e.g. N,N-dimethylformamide) and a suitable base (e.g. NaHCO$_3$), and arylation at between room temperature and reflux temperature in the presence of a suitable catalyst system (e.g. tris(dibenzylideneacetone)palladium(O) combined with tri-o-tolylphosphine), an appropriate strong base (e.g. sodium tert-butoxide) is and a reaction-inert solvent (e.g. toluene).

2. Compounds of formula I wherein Het$^1$ represents the 5-membered ring of a benzimidazole, optionally substituted in the 2-position by T$^a$, wherein T$^a$ is as hereinbefore defined provided that it does not represent C$_{1-6}$ alkoxy or C$_{1-6}$ haloalkoxy, may be prepared by reaction of a corresponding compound of formula II, as hereinbefore defined, with a compound of formula XII,

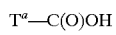
    T$^a$—C(O)OH      XII or a suitable (e.g. carboxylic acid) derivative thereof (e.g. an acid halide or an anhydride), wherein T$^a$ is as hereinbefore defined provided that it does not represent C$_{1-6}$ alkoxy or C$_{1-6}$ haloalkoxy, for example at between room temperature and 250° C.

3. Compounds of formula I wherein Het$^1$ represents the 5-membered ring of a benzimidazole, optionally substituted in the 2-position by a hydroxy group, may be prepared by reaction of a corresponding compound of formula II, as hereinbefore defined, with a suitable derivative of carbonic acid (e.g. urea), for example at between room and reflux temperature in the presence of a suitable solvent (e.g. N,N-dimethylformamide).

4. Compounds of formula I wherein Het$^1$ represents the 5-membered ring of a benzimidazole, substituted in the 2-position by a N(H)S(O)$_2$R$^6$ group, wherein R$^6$ is as hereinbefore defined, may be prepared by reaction of a corresponding compound of formula II, as hereinbefore defined, with a compound of formula XIII, (L$^2$)$_2$C=NS(O)$_2$R$^6$      XIII wherein L$^2$ represents a leaving group (such as halo) and R$^6$ is as hereinbefore defined, for example at between room and reflux temperature in the presence of a reaction-inert solvent (e.g. toluene).

5. Compounds of formula I wherein Het$^1$ represents the 5-membered ring of a benzimidazole, substituted in the 2-position by an amino group, may be prepared by hydrolysis of a corresponding compound of formula I in which Het$^1$ represents the 5-membered ring of a benzimidazole substituted in the 2-position by a N(H)S(O)$_2$R$^6$ group, wherein R$^6$ is as hereinbefore defined, for example under conditions known to those skilled in the art.

6. Compounds of formula I wherein Het$^1$ represents the 5-membered ring of a benzotriazole may be prepared by reaction of a corresponding compound of formula II, as hereinbefore defined, with a suitable source of the nitrosonium cation (e.g. sodium nitrite combined with concentrated HCl), for example at between −10° C. and room temperature in the presence of a reaction-inert solvent (e.g. a lower alkyl alcohol such as ethanol).

7. Compounds of formula I wherein Het$^1$ represents the 5-membered ring of an indole may be prepared by cyclisation of a corresponding compound of formula XIV,

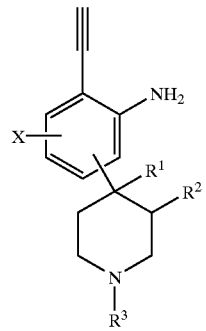

XIV wherein R$^1$, R$^2$, R$^3$ and X are as hereinbefore defined, for example at between room and reflux temperature in the presence of a suitable activator (e.g. copper(I) iodide) and a reaction-inert solvent (e.g. N,N-dimethylformamide).

Compounds of formula XIV may be prepared by reaction of a corresponding compound of formula XV,

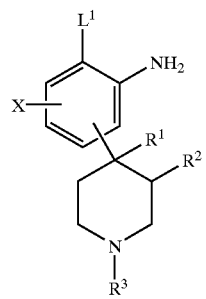

XV wherein R$^1$, R$^2$, R$^3$, L$^1$ and X are as hereinbefore defined, with acetylene, for example at between room and reflux temperature in the presence of a suitable catalyst system (e.g. bis(triphenylphosphine)palladium(II) chloride combined with copper(I) iodide) and an appropriate organic base (e.g. triethylamine).

Compounds of formula XV in which L$^a$ represents chloro, bromo or iodo may be prepared by reaction of a corresponding compound of formula V, as hereinbefore defined, with a halogen under conditions known to those skilled in the art (e.g. by reaction with a solution of the halogen in acetic acid).

8. Compounds of formula I wherein Het$^1$ represents the 5-membered ring of a benzoxazole or benzothiazole, optionally substituted in the 2-position by T$^a$, wherein T$^a$ is as hereinbefore defined, may be prepared by reaction of a corresponding compound of formula XVI,

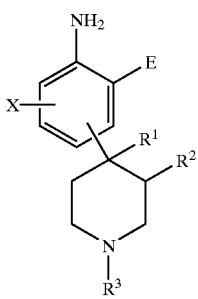

XVI wherein E represents OH or SH, and $R^1$, $R^1$, $R^3$ and X are as hereinbefore defined, with a compound of formula III or a compound of formula XII, as hereinbefore defined, for example at between room and reflux temperature in the presence of a reaction-inert solvent (e.g. xylene) and (as appropriate) a suitable catalyst (e.g. pyridinium para-toluenesulfonate) or a suitable base (e.g. triethylamine).

Compounds of formula XVI may be prepared by reduction of a corresponding compound of formula XVII,

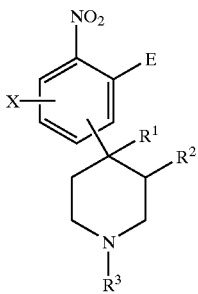

XVII wherein $R^1$, $R^2$, $R^3$, E and X are as hereinbefore defined, under conditions known to those skilled in the art (e.g. under conditions such as those described hereinbefore for the production of compounds of formula II).

Compounds of formula XVII may be prepared by nitration of a corresponding compound of formula XVIII,

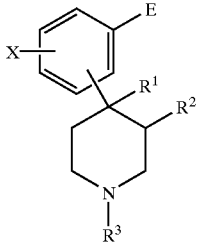

XVIII wherein $R^1$, $R^2$, $R^3$, E and X are as hereinbefore defined, for example under nitration conditions known to those skilled in the art (e.g. under conditions such as those described hereinbefore for the production of compounds of formula IV).

9. Compounds of formula I wherein $Het^1$ represents the 5-membered ring of a benzoxazole or benzothiazole, optionally substituted in the 2-position with an OH group, may be prepared by reaction of a corresponding compound of formula XVI, as hereinbefore defined, with a suitable derivative of carbonic acid (e.g. 1,1'-carbonyldiimidazole), for example at between 0° C. and reflux temperature in the presence of a reaction-inert solvent (e.g. N,N-dimethylformamide).

10. Compounds of formula I wherein $R^3$ represents $C_1$ alkyl optionally substituted by $C_{3-8}$ cycloalkyl, $Het^2$, aryl, adamantyl, (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified hereinbefore in respect to $R^3$), which alkyl, alkenyl or alkynyl groups are attached to the piperidine nitrogen atom via a $CH_2$ group, wherein $Het^2$ is as hereinbefore defined, may be prepared by reduction of a corresponding compound of formula XIX,

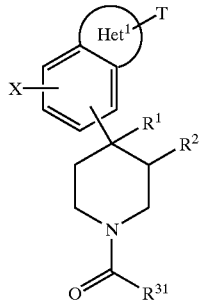

XIX wherein $R^{31}$ represents H, $C_{3-8}$ cycloalkyl, $Het^2$, aryl, adamantyl, (which latter two groups are optionally substituted by one or more substituents selected from OH, nitro, amino, halo, CN, $CH_2CN$, $CONH_2$, C1-4 alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{8c}$, $S(O)_nR^{8d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{9a})S(O)_2R^{10}$, $Het^2$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), —W—$A^1$—$N(R^{9b})(R^{9c})$, and $R^1$, $R^2$, $R^{8c}$, $R^{8d}$, $R^{9a}$ to $R^{9c}$, $R^{10}$, $Het^1$, $Het^2$, n, W, $A^1$, T and X are as hereinbefore defined, using a suitable reducing agent (e.g. lithium aluminium hydride or a borane derivative), for example as described hereinbefore.

Compounds of formula XIX may be prepared by reaction of a corresponding compound of formula XX,

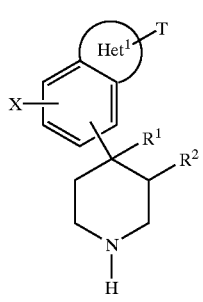

XX wherein Het¹, R¹, R², T and X are as hereinbefore defined with a compound of formula XXI, $$R^{31}CO_2H \qquad \qquad XXI$$

or a suitable (e.g. carboxylic acid) derivative thereof (e.g. an acid halide or anhydride), wherein $R^{31}$ is as hereinbefore defined, using coupling conditions known to those skilled in the art.

Compounds of formulae XIX and XX may be prepared from appropriate precursors by analogy with methods disclosed herein that describe the formation of a Het¹ group.

11. Compounds of formula I may be prepared by reaction of a corresponding compound of formula XX, as hereinbefore defined, with a compound of formula XI, as hereinbefore defined, under conditions that are known to those skilled in the art, for example as described hereinbefore in respect of the production of compounds of formula VIII.

12. Compounds of formula I wherein $R^3$ represents $C_1$ alkyl, which, in place of being optionally substituted by the substituents as defined hereinbefore, is instead optionally substituted by $R^{31}$, wherein $R^{31}$ is as hereinbefore defined, may be prepared by reaction of a corresponding compound of formula XX, as hereinbefore defined, with a compound of formula XXII, $$R^{31}CHO \qquad \qquad XXII$$

wherein $R^{31}$ is as hereinbefore defined, for example in the presence of a suitable reducing agent (e.g. sodium borohydride, sodium cyano-borohydride or sodium triacetoxyborohydride) and an appropriate solvent (e.g. methanol).

13. Compounds of formula I wherein $R^3$ is a $C_{1-10}$ alkyl, $C_{4-10}$ alkenyl or $C_{4-10}$ alkynyl group that is fully saturated from 1- to 3-C (relative to the piperidine N-atom), and which $R^3$ group is substituted at 2-C (relative to the piperidine N-atom) by $S(O)R^{8d}$, $S(O)_2R^{8d}$, alkanoyl, cycloalkanoyl, alkoxy carbonyl, CN, —C(O)—A¹—N($R^{9b}$)($R^{9c}$), —(O)—A¹—N($R^{9b}$)($R^{9c}$), or —S(O)₂—A¹—N($R^{9b}$)($R^{9c}$), wherein $R^{8d}$, $R^{9b}$, $R^{9c}$ and A¹ are as hereinbefore defined, may be prepared by reaction of a corresponding compound of formula XX, as hereinbefore defined, with a compound of formula XXIII, $$R^{3a}—Z \qquad \qquad XXIII$$

wherein $R^{3a}$ represents $R^3$ as hereinbefore defined except that it does not represent aryl, and that the $R^{3a}$ chain contains an additional carbon-carbon double bond α,β to the Z-substituent, and Z represents $S(O)R^{8d}$, $S(O)_2R^{8d}$, alkanoyl, cycloalkanoyl, alkoxy carbonyl, CN, —C(O)—A¹—N($R^{9b}$)($R^{9c}$), —S(O)—A¹—N($R^{9b}$)($R^{9c}$), or —S(O)₂—A¹—N($R^{9b}$)($R^{9c}$), wherein $R^{8d}$, $R^{9b}$, $R^{9c}$ and A¹ are as hereinbefore defined, for example at between room and reflux temperature in the presence of a reaction-inert solvent (e.g. THF).

Compounds of formulae III, IX, X, XI, XII, XIII, XV (in which L¹ does not represent chloro, bromo or iodo), XVIII, XXI, XXII, XXIII and derivatives thereof, when not commercially available or not subsequently described, may be obtained either by analogy with the processes described herein, or by conventional synthetic procedures, in accordance with standard techniques, from readily available starting materials using appropriate reagents and reaction conditions.

Compounds of formula I, XIX and XX containing other Het¹ rings (in particular, 6- and 7-membered rings) may obtained by analogy with the processes described herein. For example, 7-membered Het¹ rings containing 2 nitrogen atoms may be prepared by analogy with process 2 described hereinbefore. Other Het¹ rings, for example 7-membered Het¹ rings containing 4 nitrogen atoms, may be made by methods known in the art such as those described in Comprehensive Heterocyclic Chemistry II, edited by A R Katritsky, C W Rees and E F V Scriven, 1st Edition, Elsevier Science Ltd. (1996), or by the methods described in The Chemistry of Heterocyclic Compounds, by A Weissberger (John Wiley and Sons), Volumes 5 (1953), 33 (1978) and 50 (1991), the disclosures in which documents are hereby incorporated by reference.

It will be appreciated by those skilled in the art that the compounds delivered by the aforementioned processes can be further modified by interconverting the substituents on the aromatic moieties to other desired substituents (see, for example, Comprehensive Heterocyclic Chemistry II, edited by A R Katritsky, C W Rees and E F V Scriven, 1st Edition, Elsevier Science Ltd. (1996)). For example, nitro may be reduced to amino, OH may be alkylated to give alkoxy, alkoxy may be hydrolysed to OH, alkenes may be hydrogenated to alkanes, halo may be hydrogenated to H, etc. Substituents on alkyl groups in the above-mentioned compounds may also be introduced, removed and interconverted, using techniques which are well known to those skilled in the art.

In some cases it is possible to introduce further substituents into the compounds of formula I directly. For example, chlorination of the phenyl group of compounds of formula I, may be performed by reaction with a solution of chlorine in acetic acid.

The skilled person will also appreciate that these, and other, various standard substituent or functional group interconversions and transformations within certain compounds of formula I will provide other compounds of formula I.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, OH, amino and carboxylic acid. Suitable protective groups for oxo include acetals, ketals (e.g. ethylene ketals) and dithianes. Suitable protective groups for OH include trialkylsilyl and diarylalkylsilyl groups (e.g. tert-butyldimethylsilyl, tert-butyldiphenylsilyl or trimethylsilyl) and tetrahydropyranyl. Suitable protective groups for amino include tert-butyloxycarbonyl, 9-fluorenylmethoxycarbonyl, benzyloxycarbonyl or ethanoyl. Suitable protective groups for carboxylic acid include $C_{1-6}$ alkyl or benzyl esters. Suitable protective groups for terminal alkynes include trialkylsilyl and diarylalkylsilyl groups (e.g. tert-butyldimethylsilyl, tert-butyldiphenyl-silyl or trimethylsilyl).

The protection and deprotection of functional groups may take place before or after any of the reaction steps described hereinbefore.

Protective groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I. For example, biolabile groups may be placed on functional groups of compounds of formula I (e.g. an NH functionality in a $Het^1$ group), and in the case of 5- or 6-membered $Het^1$ rings containing NH functionalities, such biolabile derivatives may be preferred.

All protected and biolabile derivatives, and prodrugs, of compounds of formula I are included within the scope of the invention.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

The compounds of the invention are useful because they possess pharmacological activity in animals, especially mammals including humans. They are therefore indicated as pharmaceuticals and, in particular, for use as animal medicaments.

According to a further aspect of the invention there is provided the compounds of the invention for use as medicaments, such as pharmaceuticals and animal medicaments.

By the term "treatment", we include both therapeutic (curative) or prophylactic treatment.

In particular, the compounds of the invention have been found to be useful in the treatment of diseases mediated via opiate receptors, which diseases include irritable bowel syndrome; constipation; nausea; vomiting; pruritus; and conditions characterised by pruritus as a symptom.

Thus, according to a further aspect of the invention there is provided the use of the compounds of the invention in the manufacture of a medicament for the treatment of a disease mediated via an opiate receptor. There is further provided the use of the compounds of the invention in the manufacture of a medicament for the treatment of irritable bowel syndrome; constipation; nausea; vomiting; pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing a disease mediated via an opiate receptor. There is further provided a method of treating irritable bowel syndrome; constipation; nausea; vomiting; pruritus or a medical condition characterised by pruritus as a symptom in an animal (e.g. a mammal), which comprises administering a therapeutically effective amount of a compound of the invention to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterials, e.g. enroflaxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of diseases mediated via opiate receptors.

The skilled person will also appreciate that compounds of the invention may be taken as a single dose on an "as required" basis (i.e. as needed or desired).

Thus, according to a further aspect of the invention there is provided a pharmaceutical, or veterinary, formulation including a compound of the invention in admixture with a pharmaceutically, or veterinarily, acceptable adjuvant, diluent or carrier.

Compounds of the invention may also have the advantage that, in the treatment of human and/or animal patients, they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test method.

Biological Test

Compounds of the present invention have been found to display activity in binding assays selective for the mu opioid receptor in dog brain. The assays were conducted by the following procedure.

Laboratory bred beagles were used as a source of dog brain tissue. Animals were euthanised, their brains removed and the cerebellum discarded. The remaining brain tissue was sectioned into small pieces approximately 3 g in weight and homogenised in 50 mM Tris pH 7.4 buffer at 4° C. using a Kinematica Polytron™ tissue homogeniser. The resulting homogenate was centrifuged at 48,400×g for 10 minutes and the supernatant discarded. The pellet was resuspended in Tris buffer and incubated at 37° C. for 10 minutes. Centrifugation, resuspension and incubation steps were repeated twice more, and the final pellet was resuspended in Tris buffer and stored at −80° C. Membrane material prepared in this manner could be stored for up to four weeks prior to use.

For mu assays, increasing concentrations of experimental compound, ($5 \times 10^{-12}$ to $10^{-5}$ M), Tris buffer and $^3$H ligand, ([D-Ala$^2$,N-Me-Phe$^4$,Gly-ol$^5$]-Enkephalin, DAMGO), were combined in polystyrene tubes. The reaction was initiated by the addition of tissue, and the mixture was incubated at room temperature for 90 minutes. The reaction was terminated by rapid filtration using a Brandel Cell Harvester™ through Betaplate™ GF/A glass fibre filters pre-soaked in 50 mM Tris pH 7.4, 0.1% polyethylenimine buffer. The filters were then washed three times with 0.5 mL ice-cold Tris pH 7.4 buffer. Washed filters were placed in bags and Starscint™ scintillant added. Bags containing the filters and scintillant were heat sealed and counted by a Betaplate™ 1204 beta counter.

Duplicate samples were run for each experimental compound and the data generated was analysed using IC$_{50}$ analysis software in Graphpad Prism.

Ki values were calculated using Graphpad Prism according to the following formula:

$$Ki = IC_{50}/1 + [^3H\ ligand]/K_D$$

where IC$_{50}$ is the concentration at which 50% of the $^3$H ligand is displaced by the test compound and K$_D$ is the dissociation constant for the $^3$H ligand at the receptor site.

The invention is illustrated by the following Examples and Preparations in which the following abbreviations may be used:

APCI=atmospheric pressure chemical ionisation
br (in relation to NMR)=broad
CI=chemical ionisation
DMF=N,N-dimethylformamide
DMSO=dimethylsulfoxide
d (in relation to time)=day
d (in relation to NMR)=doublet
dd (in relation to NMR)=doublet of doublets
EtOAc=ethyl acetate
EtOH=ethanol
h=hour(s)
m (in relation to NMR)=multiplet
MeOH=methanol
min=minute
q (in relation to NMR)=quartet
q$^i$ (in relation to NMR)=quintet
s (in relation to NMR)=singlet
t (in relation to NMR)=triplet
THF=tetrahydrofuran For purifications by HPLC, combination and evaporation of appropriate fractions, determined by analytical HPLC, provided the desired compounds as acetate salts.

Analytical HPLC conditions used to highlight appropriate fractions were Phenomenex Magellanm column, 4.6×150 mm, packed with 5 $\mu$ $C_{18}$ silica, eluting with a gradient of acetonitrile:0.1 M aqueous heptanesulfonic acid (10:90 to 90:10 over 30 min, followed by a further 10 min at 90:10) at 1 mL per minute. Column oven temperature was 40° C., and ultraviolet detection of components was made at 220 nM.

When column chromatography is referred to this usually refers to a glass column packed with silica gel (40–63 $\mu$m). Pressure of ~165 kPa is generally applied and the ratio of crude product:silica gel required for purification is typically 50:1. Alternatively, an Isolute™ SPE (solid phase extraction) column or Waters Sep-Pak™ cartridge packed with silica gel may be used under atmospheric pressure. The ratio of crude product to silica gel required for purification is typically 100:1.

The hydrochloride salt may be made by methods commonly known to those skilled in the art of synthetic chemistry. Typically, to a solution of free base in dichloromethane (1 g:100 mL) was added ethereal hydrochloric acid (1.0 M, 1.2 equivalent), the excess solvent was decanted off and the remaining precipitate was washed three times with ether and then dried in vacuo.

Nuclear magnetic resonance (NMR) spectral data were obtained using a Brucker AC3000, Brucker AM300, Varian Unity 300 or Varian Unity 400 spectrometer, the observed chemical shifts ($\delta$) being consistent with the proposed structures. Mass spectral (MS) data were obtained on a Finnigan Masslab Navigator, a Fisons Instruments Trio 1000, a Fisons Instruments Trio 1000 APCI, or a Micromass Platform LC spectrometer. The calculated and observed ions quoted refer to the isotopic composition of lowest mass. HPLC means high performance liquid chromatography. Room temperature means 20 to 25° C.

EXAMPLES

Example 1

Trans-(±)-5-(1-Hexyl-3,4-dimethyl-4-piperidinyl)-1H-1,2,3-benzotriazole

To a solution of trans-(±)-N-[2-amino-5-(1-hexyl-3,4-dimethyl-4-piperidinyl)phenyl]acetamide (Preparation 3, 53 mg, 0.153 mmnol) in ethanol (1 mL) was added concentrated hydrochloric acid (0.2 mL) and the mixture cooled in an ice bath. A solution of sodium nitrite (21 mg, 0.31 mmol) in water (0.1 mL) was added dropwise and stirring continued for 3 hours at this temperature. A further portion of hydrochloric acid (0.1 mL) was added and the reaction refluxed for 3 hours. The reaction mixture was cooled and diluted with ethyl acetate (100 mL) and water (50 mL), and then washed with saturated sodium bicarbonate solution (50 mL). The separated organic phase was washed with brine (25 mL) and both aqueous phases extracted with ethyl acetate (25 mL). The combined organics were dried ($MgSO_4$) then concentrated in vacuo. The residue was triturated with hexane twice then dried on a vacuum pump to give the benzotriazole (44 mg) as a pale yellow solid.

NMR $\delta_H$(300 MHz, $CDCl_3$) (selected data): 0.70 (3H, d), 0.85 (3H, m), 1.40 (3H, s), 7.40 (1H, d), 7.70 (1H, s) and 7.85 (1H, d). MS (Thermospray): M/Z ($MH^+$) 315.3; $C_{19}H_{30}N_4$+H requires 315.5.

Example 2

Trans-(±)-5-(1-Hexyl-3,4-dimethyl-4-piperidinyl)-1H-benzimidazole

A solution of trans-(±)-4-(1-hexyl-3,4-dimethyl-4-piperidinyl)-1,2-benzenediamine (Preparation 5, 150 mg, 0.494 mmol) in 90% formic acid (1.0 mL) was heated to 100° C. for 2 hours. The reaction was diluted with water (50 mL) and poured into ethyl acetate (50 mL) and 2 N sodium hydroxide (25 mL). The organic layer was washed with brine (25 mL) and both aqueous layers extracted with ethyl acetate (50 mL). The combined organics were dried ($MgSO_4$) and then concentrated in vacuo to give the benzimidazole (130 mg) as a light brown oil. This was dissolved in diethyl ether (1.0 mL) and treated with 1 N HCl in diethyl ether (0.46 mL, 0.46 mmol), which was added dropwise. The solvent was removed in vacuo to give the hydrochloride as a light brown solid.

NMR $\delta_H$(300 MHz, $CDCl_3$) (selected data from free base): 0.80 (3H, d), 0.90 (3H, m), 1.35 (3H, s), 7.25 (1H, d), 7.50 (1H, s), 7.60 (1H, d) and 8.00 (1H, s). MS (Thermospray): M/Z ($MH^+$) 313.8; $C_{20}H_{30}N_3$+H requires 313.5.

Example 3

Trans-(±)-2-Methyl-5-(1-hexyl-3,4-dimethyl-4-piperidinyl)-1H-benzimidazole

A solution of trans-(±)-N-[2-amino-5-(1-hexyl-3,4-dimethyl-4-piperidinyl)-phenyl]acetamide (Preparation 3, 150 mg, 0.434 mmol) in acetic acid (2.0 mL) was heated to reflux for 2 hours. The reaction was diluted with water (25 mL) and ethyl acetate (50 mL) then washed with 2 N sodium hydroxide solution (50 mL). The separated organic phase was washed with brine (50 mL). Both aqueous phases were extracted with ethyl acetate (50 mL) and the combined organics dried ($MgSO_4$) then concentrated in vacuo. The crude residue was chromatographed on Merck 230–400 mesh silica gel (10 g) using ethyl acetate:2 N ammonia in methanol (95:5) as the eluant to give the benzimidazole (71 mg) as a pale yellow oil. This was dissolved in diethyl ether (1 mL) and treated with 1 N HCl in diethyl ether (0.2 mL, 0.2 mmol). The solvent was removed in vacuo to give the hydrochloride as pale brown solid.

NMR $\delta_H$(300 MHz, $CDCl_3$) (selected data from free base): 0.75 (3H, d), 0.85 (3H, m), 1.35 (3H, s), 2.60 (3H, s), 7.20 (1H, d) and 7.40–7.50 (2H, br s). MS (CI): M/Z ($MH^+$) 328.5; $C_{21}H_{33}N_3$+H requires 328.5.

Example 4

Trans-(±)-2-(Trifluoromethyl)-5-(1-hexyl-3,4-dimethyl-4-piperidinyl)-1H-benzimidazole A solution of trans-(±)-4-(1-hexyl-3,4-dimethyl-4-piperidinyl)-1,2-benzenediamine (Preparation 5, 25 mg, 82 $\mu$mol) in trifluoroacetic acid (1 mL) was refluxed for 2 hours. The cooled reaction was diluted with water (25 mL) and ethyl acetate (50 mL) then washed with 2 N sodium hydroxide solution (25 mL). The organic layer was washed with brine (25 mL) and both aqueous layers back-extracted with ethyl acetate (25 mL). The combined organics were dried ($MgSO_4$) and then concentrated in vacuo. The residue was chromatographed on Merck 230–400 mesh silica gel (10 g) using ethyl acetate:methanol (90:10) as eluant to give the benzimidazole (29 mg) as a pale yellow oil. This was dissolved in diethyl ether (1 mL) and treated with 1 N HCl in diethyl ether (84 $\mu$L, 84 $\mu$mol). The solvent was removed in vacuo to give the hydrochloride as a light brown solid.

NMR $\delta_H$(300 MHz, $CDCl_3$) (selected data from free base): 0.75 (3H, d), 0.85 (3H, m), 1.40 (3H, s), 7.35 (1H, d), 7.55 (1H, s) and 7.65 (1H, d). MS (CI): M/Z ($MH^+$) 382.4; $C_{21}H_{30}F_3N_3$+H requires 382.5.

Example 5

Trans-(±)-6-(1-Hexyl-3,4-dimethyl-4-piperidinyl)-1H-indole

To a solution of trans-(±)-2-[2-(trimethylsilyl)ethynyl]-5-(1-hexyl-3,4-dimethyl-4-piperidinyl)aniline (Preparation 7, 211 mg, 0.55 mmol) in N,N-dimethylformamide (2 mL) under nitrogen was added copper(I) iodide (208 mg, 1.09 mmol) and the reaction mixture heated to 100° C. for 1.5 hours. The cooled reaction was diluted with diethyl ether and filtered through Celite®. The filtrate was washed with brine and the separated aqueous layer extracted with diethyl ether (3×50 mL). The combined organics were dried ($MgSO_4$) and concentrated in vacuo. The residue was chromatographed on Merck 230–400 mesh silica gel using a gradient of dichloromethane:ethanol:ammonium hydroxide (300:8:1 to 200:8:1) to give the indole (51 mg) as an oil. This was dissolved in dichloromethane and treated with 1 N HCl in diethyl ether (2 mL). The solvent was removed in vacuo to give the hydrochloride as a light yellow solid.

NMR $\delta_H$(300 MHz, $CDCl_3$) (selected data from free base): 0.80 (3H, s), 0.90 (3H, m), 1.35 (3H, s), 6.50 (1H, s), 7.10 (1H, d), 7.15 (1H, m), 7.25 (1H, m), 7.60 (1H, d) and 8.05 (1H, br s). MS (CI): M/Z (MH$^+$) 313.4; $C_{21}H_{32}N_2$+H requires 313.5.

Example 6

Trans-(±)-2-Isopropyl-5-(1-hexyl-3,4-dimethyl-4-piperidinyl)-1H-benzimidazole A solution of trans-(±)-4-(1-hexyl-3,4-dimethyl-4-piperidinyl)-1,2-benzenediamine (Preparation 5, 36 mg, 0.119 mmol) in isobutyric acid (1 mL) was refluxed for 4 hours. The cooled reaction was diluted with water (25 mL) and ethyl acetate (50 mL) then washed with 2 N sodium hydroxide solution (25 mL). The organic layer was washed with brine (25 mL) and both aqueous layers back-extracted with ethyl acetate (25 mL). The combined organics were dried ($MgSO_4$) then concentrated in vacuo. The residue was chromatographed on Merck 230–400 mesh silica gel (10 g) using ethyl acetate: 2 N ammonia in methanol (97:3) as eluant to give the benzimidazole (3 mg) as a colourless oil. This was dissolved in diethyl ether (0.5 mL) and treated with 1 N HCl in diethyl ether (9 µL, 9 µmol). The solvent was removed in vacuo to give the hydrochloride as a reddish solid.

NMR $\delta_H$(300 MHz, $CDCl_3$) (selected data from free base): 0.80 (3H, d), 0.90 (3H, m), 1.30 (3H, s), 1.45 (6H, d) and 6.70–7.20 (3H, m). MS (Thermospray): M/Z (MH$^+$) 356.2; $C_{23}H_{37}N_3$+H requires 356.5.

Example 7

Trans-(±)-2-Methoxy-5-(1-hexyl-3,4-dimethyl-4-piperidinyl)-1H-benzimidazole

A mixture containing trans-(±)-4-(1-hexyl-3,4-dimethyl-4-piperidinyl)-1,2-benzenediamine (Preparation 5, 33 mg, 0.109 mmol), tetramethoxy-methane (1 mL) and glacial acetic acid (7 mL) was stirred at room temperature for 2 hours then refluxed for a further 2 hours. The reaction mixture was concentrated in vacuo, dissolved in ethyl acetate (50 mL) and then washed with saturated potassium carbonate solution (25 mL) and brine (25 mL). Each of the aqueous phases were extracted with ethyl acetate (25 mL) and the combined organics dried ($MgSO_4$) and then concentrated in vacuo. The residue was chromatographed on Merck 230–400 mesh silica gel (10 g) using ethyl acetate:2 N ammonia in methanol (97:3) as eluant to give the benzimidazole (5 mg) as a colourless oil. NMR $\delta_H$(300 MHz, $CDCl_3$) (selected data): 0.80 (3H, d), 0.90 (3H, s), 1.35 (3H, s), 4.15 (3H, s) and 6.85–7.10 (3H, m). MS (CI): M/Z (MH$^+$) 344.4; $C_{21}H_{33}N_3O$+H requires 344.5.

Example 8

Trans-(±)-2-Cyclobutyl-5-(1-hexyl-3,4-dimethyl-4-piperidinyl)-1H-benzimidazole A stirred solution of trans-(±)-4-(1-hexyl-3,4-dimethyl-4-piperidinyl)-1,2-benzenediamine (Preparation 5, 58 mg, 0.19 mmol) in cyclobutane-carboxylic acid (1 mL, 10 mmol) was heated at 145° C. for 2 hours. The cooled reaction mixture was treated with 2 N sodium hydroxide solution (20 mL) and back-extracted with dichloromethane. The combined organics were dried ($MgSO_4$) and then concentrated in vacuo to give a black oil. The crude residue was chromatographed on Merck 230–400 mesh silica gel (10 g) using ethyl acetate:2 N ammonia in methanol (99:1) as eluant to give the benzimidazole (47 mg) as a pale yellow oil. The oil was dissolved in dry diethyl ether (1 mL) and treated with a solution of 1 N HCl in diethyl ether (128 µL, 128 µmol). The solvent was removed in vacuo to give the hydrochloride as a purple solid.

NMR $\delta_H$(300 MHz, $CDCl_3$) (selected data from free base): 0.75 (d, 3H), 0.85 (m, 3H), 1.30 (s, 3H), 3.75 (q$^i$, 1H), 7.18 (m, 2H), 7.25 (s, 1H) and 7.50 (br s, 1H). MS (Thermospray): M/Z (MH$^+$) 368.3; $C_{24}H_{37}N_3$+H requires 368.3.

Example 9

Trans-(±)-2-Benzyl-5-(1-hexyl-3,4-dimethyl-4-piperidinyl)-1H-benzimidazole

A stirred solution of trans-(±)-4-(1-hexyl-3,4-dimethyl-4-piperidinyl)-1,2-benzenediamine (Preparation 5, 48 mg, 0.16 mmol) in phenylacetic acid (1 mL, 8 mmol) was heated at 190° C. for 2 hours. The cooled reaction mixture was treated with 2 N sodium hydroxide solution (20 mL) and back-extracted with dichloromethane. The combined organics were dried ($MgSO_4$) then concentrated in vacuo to give a black oil. The oil was chromatographed on Merck 230–400 mesh silica gel (10 g) using ethyl acetate:2 N ammonia in methanol (99:1) as eluant to give the benzimidazole (31 mg) as a pale yellow oil. The oil was dissolved in dry diethyl ether (1 mL) and treated with a solution of 1 N HCl in diethyl ether (77 µL, 77 µmol). The solvent was removed in vacuo to give the hydrochloride as a white solid.

NMR $\delta_H$(300 MHz, $CDCl_3$) (selected data from free base): 0.75 (d, 3H), 0.90 (m, 3H), 1.30 (s, 3H), 4.25 (m, 2H), 7.10–7.40 (m, 8H) and 7.60 (br s, 1H). MS (Thermospray): M/Z (MH$^+$) 404.2; $C_{27}H_{37}N_3$+H requires 404.3.

Example 10

Trans-(±)-2-Cyclopentyl-5-(1-hexyl-3,4-dimethyl-4-piperidinyl)-1H-benzimidazole A stirred solution of trans-(±)-4-(1-hexyl-3,4-dimethyl-4-piperidinyl)-1,2-benzenediamine (Preparation 5, 49 mg, 0.161 mmol) in cyclopentane-carboxylic acid (1 mL) was heated at reflux for 2 hours. The cooled reaction was diluted with ethyl acetate (25 mL) and washed with 2 N sodium hydroxide solution (25 mL). The separated organic phase was washed with brine (25 mL) and each of the separated aqueous phases extracted with ethyl acetate (25 mL). The combined organics were dried (MgSO$_4$) and then concentrated in vacuo. The crude residue was chromatographed on Merck 230–400 mesh silica gel (10 g) using ethyl acetate:2 N ammonia in methanol (99:1) as eluant to give the benzimidazole (19 mg) as a pale yellow oil. The oil was dissolved in diethyl ether (1 mL) and treated with a solution of 1 N HCl in diethyl ether (55 µL, 55 µmol). The solvent was removed in vacuo to give the hydrochloride as a purple solid.

NMR $\delta_H$(300 MHz, CDCl$_3$) (selected data from free base): 0.75 (3H, d), 0.85 (3H, m), 1.30 (3H, s), 3.30 (1H, q), 7.20 (1H, d) and 7.60 (2H, m). MS (Thermospray): M/Z (MH$^+$) 382.3; C$_{25}$H$_{39}$N$_3$+H requires 382.6.

Example 11

Trans-(±)-2-(Difluoromethyl)-5-(1-hexyl-3,4-dimethyl-4-piperidinyl)-1H-benzimidazole A solution of trans-(±)-4-(1-hexyl-3,4-dimethyl-4-piperidinyl)-1,2-benzenediamine (Preparation 5, 55 mg, 0.181 mmol) in difluoroacetic acid (1 mL) was refluxed for 4 hours. The cooled reaction was diluted with water (25 mL) and ethyl acetate (50 mL) then washed with 2 N sodium hydroxide solution (25 mL). The organic layer was washed with brine (25 mL) and both aqueous layers back-extracted with ethyl acetate (25 mL). The combined organics were dried (MgSO$_4$) then concentrated in vacuo. The residue was chromatographed on Merck 230–400 mesh silica gel (10 g) using ethyl acetate:2 N ammonia in methanol (97:3) as eluant to give the benzimidazole (47 mg) as a pale yellow oil. This was dissolved in diethyl ether (1 mL) and treated with 1 N HCl in diethyl ether (142 µL, 142 µmol). The solvent was removed in vacuo to give the hydrochloride as a pale yellow solid.

NMR $\delta_H$(300 MHz, CDCl$_3$) (selected data from free base): 0.70 (3H, d), 0.85 (3H, m), 1.40 (3H, s), 6.85 (1H, t), 7.30 (1H, d) and 7.60 (2H, m). MS (Thermospray): M/Z (MH$^+$) 364.2; C$_{21}$H$_{31}$F$_2$N$_3$+H requires 364.5.

Example 12

Trans-(±)-2-ethyl-5-(1-Hexyl-3,4-dimethyl-4-piperidinyl)-1H-benzimidazole

A solution of trans-(±)-4-(1-hexyl-3,4-dimethyl-4-piperidinyl)-1,2-benzenediamine (Preparation 5, 55 mg, 0.181 mmol) in propionic acid (1 mL) was refluxed for 4 hours. The cooled reaction was diluted with water (25 mL) and ethyl acetate (50 mL) then washed with 2 N sodium hydroxide solution (25 mL). The organic layer was washed with brine (25 mL) and both aqueous layers back-extracted with ethyl acetate (25 mL). The combined organics were dried (MgSO$_4$) and then concentrated in vacuo. The residue was chromatographed on Merck 230–400 mesh silica gel (10 g) using ethyl acetate:2 N ammonia in methanol (99:1) as eluant to give the benzimidazole (30 mg) as a pale yellow oil. This was dissolved in diethyl ether (1 mL) and treated with 1 N HCl in diethyl ether (100 µL, 100 µmol). The solvent was removed in vacuo to give the hydrochloride as a pale yellow solid.

NMR $\delta_H$(300 MHz, CDCl$_3$) (selected data from free base): 0.75 (3H, d), 0.85 (3H, m), 1.35 (3H, s), 1.40 (3H, t), 2.90 (2H, q), 7.20 (1H, d) and 7.50 (2H, m). MS (Thermospray): M/Z (MH$^+$) 342.1; C$_{22}$H$_{34}$N$_3$+H requires 342.5.

Example 13

Trans-(±)-5-(1-Hexyl-3,4-dimethyl-4-piperidinyl)-1,3-dihydro-2H-benzimidazol-2-one A mixture of trans-(±)-4-(1-hexyl-3,4-dimethyl-4-piperidinyl)-1,2-benzenediamine (Preparation 5, 195 mg, 0.643 mmol), urea (244 mg, 4.07 mmol) and N,N-dimethylformamide (2.1 mL) was heated to reflux for 5 hours. The cooled mixture was concentrated under reduced pressure and the residue partitioned between ethyl acetate (25 mL) and water (25 mL). The organic phase was extracted with brine (25 mL) and each separated aqueous phase extracted with ethyl acetate (25 mL). The combined organics were dried (MgSO$_4$) then concentrated in vacuo. The crude product was chromatographed on Merck 230–400 mesh silica gel (10 g) using ethyl acetate:2 N ammonia in methanol (97:3) as eluant to give the benzimidazolone (30 mg) as a pale brown solid.

NMR $\delta_H$(300 MHz, CDCl$_3$) (selected data from free base): 0.75 (3H, d), 0.90 (3H, m), 3.30 (1H, br s) and 7.00 (3H, m). MS (Thermospray): M/Z (MH$^+$) 330.1; C$_{20}$H$_{30}$N$_3$O+H requires 330.5.

Example 14

Trans-(±)-N-[5-(1-Hexyl-3,4-dimethyl-4-piperidinyl)-1H-benzimidazol-2-yl]methanesulfonamide To a solution of trans-(±)-4-(1-hexyl-3,4-dimethyl-4-piperidinyl)-1,2-benzenediamine (Preparation 5, 1.05 g, 3.46 mmol) in toluene (30 mL) under an atmosphere of nitrogen was added a solution of N-methanesulfonylcarbonimidic acid dichloride ([Neidlein and Haussmann, *Tetrahedron Lett.*, 1965, 1753] 0.61 g, 3.46 mmol) in toluene (5 mL). The reaction was heated at 85° C. for 5 hours then cooled to room temperature and allowed to stand under an atmosphere of nitrogen overnight. The reaction mixture was concentrated in vacuo and the residue partitioned between dichloromethane (50 mL) and saturated sodium bicarbonate solution (50 mL), which mixture was stirred for 1 hour. The organic layer was separated and the aqueous washings were extracted with dichloromethane (2×50 mL). The combined organics were dried (Na$_2$SO$_4$) and concentrated in vacuo to give a dark green-black solid. The residue was chromatographed on Merck 230–400 mesh silica gel (50 g) eluting hexane:ethyl acetate (40:60 to 20:80), basified with 3 drops of concentrated ammonium hydroxide, to give the sulfonamide (495 mg) as a yellow solid.

NMR $\delta_H$(300 MHz, CD$_3$OD) (selected data from free base): 0.75 (3H, d), 0.90 (3H, t), 1.30–1.40 (9H, m), 1.45–1.6 (2H, m), 1.70 (1H, m), 2.10 (1H, m), 2.25–2.50 (4H, m), 2.55–2.70 (2H, m), 2.85 (1H, m), 3.00 (3H, s) and 7.15–7.25 (3H, m). MS (Electrospray): M/Z (MH$^+$) 407.2; C$_{21}$H$_{34}$N$_4$O$_2$S+H requires 407.3.

Example 15

Trans-(±)-5-(1-Hexyl-3,4-dimethyl-4-piperidinyl)-1H-benzimidazol-2-ylamine

A solution of trans-(±)-N-[5-(1-hexyl-3,4-dimethyl-4-piperidinyl)-1H-benzimidazol-2-yl]methanesulfonamide (Example 14, 150 mg, 3.22 mmol) in 48% hydrobromic acid (5 mL) and glacial acetic acid (5 mL) was refluxed for 48 hours. The reaction mixture was cooled and basified to pH 10 with 2 N sodium hydroxide solution. The product was extracted with dichloromethane (3×25 mL) and the solvent was dried (Na$_2$SO$_4$). The crude residue was chromatographed on Merck 230–400 mesh silica gel (8 g) eluting with ethyl acetate-dichloromethane (20:80). The starting material was collected from the column, before flushing with methanol:dichloromethane (40:60). The residue was concentrated in vacuo then redissolved in dichloromethane (30 mL). The solvent was dried ($Na_2SO_4$), filtered and concentrated in vacuo to give the benzimidazolamine (15 mg) as a light brown solid.

NMR $\delta_H$(300 MHz, $CD_3OD$) (selected data from free base): 0.80 (3H, d), 0.90 (3H, t), 1.80 (1H, m), 2.20 (1H, m), 2.40 (1H, m), 2.90 (1H, m), 6.95 (1H, d) and 7.10–7.20 (2H, m). MS (Electrospray): M/Z ($MH^+$) 329.2; $C_{20}H_{32}N_4$+H requires 329.3.

Example 16

Trans-(±)-2-(Trifluoromethyl)-5-[1-(3-phenylpropyl)-3,4-dimethyl-4-piperidinyl]-1H-benzimidazole A solution of trans-(±)-2-(trifluoromethyl)-5-(3,4-dimethyl-4-piperidinyl)-1H-benzimidazole (Preparation 11, 100 mg, 0.34 mmol) in N,N-dimethylformamide (3 mL) was treated with sodium bicarbonate (45 mg, 0.54 mmol) and then 1-bromo-3-phenylpropane (82 μL, 108 mg, 0.54 mmol). The reaction was heated at 80° C. for 6 hours and the solvent was removed by evaporation in vacuo. The residue was partitioned between dichloromethane and water. The organic solvent was dried ($Na_2SO_4$) and the solvent removed by evaporation in vacuo. The residue was chromatographed on Merck 230–400 mesh silica gel (5 g) using a gradient of ethyl acetate:hexane:ammonium hydroxide (39:60:1 to 49:50:1) to give the benzimidazole (28 mg) as an oil.

NMR $\delta_H$(300 MHz, $CDCl_3$) (selected data from free base): 0.70 (d, 3H), 1.40 (s, 3H) and 7.10–7.30 (m, 8H). MS (Thermospray): M/Z ($MH^+$) 416.2; $C_{24}H_{28}F_3N_3$+H requires 416.5.

Example 17

Trans-(±)-2-(Trifluoromethyl)-5-[1-(2-phenoxyethyl)-3,4-dimethyl-4-piperidinyl]-1H-benzimidazole A solution of trans-(±)-2-(trifluoromethyl)-5-(3,4-dimethyl-4-piperidinyl)-1H-benzimidazole (Preparation 11, 50 mg, 0.17 mmol) in N,N-dimethylformamide (2 mL) was treated with sodium bicarbonate (23 mg, 0.27 mmol) and then β-bromophenetole (38 mg, 0.19 mmol). The reaction was heated at 60° C. for 6 hours then stirred at room temperature overnight. The solvent was evaporated in vacuo and the residue partitioned between dichloromethane and water. The organic solvent was dried ($Na_2SO_4$) and the solvent evaporated in vacuo. The residue was chromatographed on Merck 230–400 mesh silica gel (5 g) using a gradient of ethyl acetate:hexane:ammonium hydroxide (0:99:1 to 49:50:1) to give the benzimidazole (20 mg) as an oil.

NMR $\delta_H$(300 MHz, $CDCl_3$) (selected data from free base): 0.70 (d, 3H), 1.30 (s, 3H), 3.50 (m, 1H), 4.10 (m, 2H), 4.20 (m, 1H), 6.60 (m, 2H), 6.90 (m, 4H) and 7.30 (m, 2H). MS (Thermospray): M/Z ($MH^+$) 418.4; $C_{23}H_{26}F_3N_3O$+H requires 418.5.

Example 18

Trans-(±)-2-(Trifluoromethyl)-5-[1-(3-methylphenethyl)-3,4-dimethyl-4-piperidinyl]-1H-benzimidazole A solution of trans-(±)-2-(trifluoromethyl)-5-(3,4-dimethyl-4-piperidinyl)-1H-benzimidazole (Preparation 11, 51 mg, 0.17 mmol) in N,N-dimethylformamide (2 mL) was treated with sodium bicarbonate (28 mg, 0.33 mmol) and then 1-(2-bromoethyl)-3-methylbenzene (37 mg, 0.19 mmol). The reaction was heated to 60° C. for 24 hours. The reaction mixture was cooled to room temperature and partitioned between dichloromethane (10 mL) and water (10 mL). The organic layer was dried ($Na_2SO_4$), filtered and the solvent evaporated in vacuo. The residue was chromatographed on Merck 230–400 mesh silica gel (5 g) using a gradient of ethyl acetate:hexane:ammonium hydroxide (10:89:1 to 50:49:1) to give the benzimidazole (5 mg) as an oil.

NMR $\delta_H$(300 MHz, $CDCl_3$) (selected data from free base): 0.80 (m, 3H), 1.30 (s, 3H), 2.30 (s, 3H), 3.40 (t, 1H), 6.60 (m, 2H), 7.00 (m, 3H) and 7.10–7.20 (m, 2H). MS (Thermospray): M/Z ($MH^+$) 416.4; $C_{24}H_{28}F_3N_3$+H requires 416.5.

Example 19

Trans-(±)-5-(1-Benzyl-3,4-dimethyl-4-piperidinyl)-1H-benzimidazole

A solution of trans-(±)-N-[2-amino-5-(1-benzyl-3,4-dimethyl-4-piperidinyl)phenyl]formamide (Preparation 14, 98 mg, 0.29 mmol) in formic acid (11 mL) was refluxed for 6 hours and made basic by addition of 2 N sodium hydroxide solution. The aqueous layer was washed ethyl acetate (30 mL) and the organic layer dried ($Na_2SO_4$) then concentrated in vacuo. The residue was chromatographed on Merck 230–400 mesh silica gel (10 g), using methanol:dichloromethane:ammonium hydroxide (10:89:1) as eluant to give the benzimidazole (72 mg) as an oil.

NMR $\delta_H$(300 MHz, $CDCl_3$) (selected data from free base): 0.70 (d, 3H), 1.40 (s, 3H), 2.40 (d, 2H), 2.50 (s, 2H), 2.90 (m, 1H), 3.50 (d, 1H), 3.60 (d, 1H), 7.20–7.40 (m, 7H) and 7.50–7.60 (m, 2H). MS (Thermospray): M/Z ($MH^+$) 320.8; $C_{21}H_{25}N_3$+H requires 320.5.

Example 20

Trans-(±)-5-[1-(2-Propoxyethyl)-3,4-dimethyl-4-piperidinyl]-1H-benzimidazole

A solution of trans-(±)-5-(3,4-dimethyl-4-piperidinyl)-1H-benzimidazole (Preparation 15, 30 mg, 0.13 mmol) in N,N-dimethylformamide (2 mL) was treated with 2-chloroethylpropyl ether (17 mg, 0.14 mmol) and then sodium bicarbonate (25 mg, 0.3 mmol) and a catalytic amount of sodium iodide. The mixture was heated at 60° C. for 6 hours. The reaction mixture was partitioned between sodium bicarbonate solution (10 mL) and diethyl ether (10 mL). The separated organic phase was dried ($Na_2SO_4$) and concentrated in vacuo. The title compound was purified by preparative HPLC on a Phenomenex Magellen™ column, 150 mm×21 mm; Flow 20 mL $min^{-1}$; employing UV detection at 220 nm; eluant acetonitrile:0.1 M aqueous ammonium acetate (30:70 to 95:5 over 10 minutes). MS (Thermospray): M/Z ($MH^+$) 316.3; $C_{19}H_{29}N_3O$+H requires 316.5.

Example 21

Trans-(±)-5-[1-(5-Methylhexyl)-3,4-dimethyl-4-piperidinyl]-1H-benzimidazole

A solution of trans-(±)-5-(3,4-dimethyl-4-piperidinyl)-1H-benzimidazole (Preparation 15, 30 mg, 0.13 mmol) in N,N-dimethylformamide (2 mL) was treated with 1-bromo- 5-methylhexane (25 mg, 0.14 mmol), followed by sodium bicarbonate (25 mg, 0.3 mmol). The reaction was heated to 60° C. for 6 hours. The reaction was partitioned between saturated sodium bicarbonate solution (10 mL) and diethyl ether (10 mL). The separated organic phase was dried ($Na_2SO_4$) and the solvent was removed by evaporation in vacuo. The title compound was purified by preparative HPLC on a Phenomenex Magellen™ column, 150 mm×21 mm; Flow 20 mL min$^{-1}$; employing UV detection at 220 nm; eluant acetonitrile:0.1 M aqueous ammonium acetate (30:70 to 95:5 over 10 minutes). MS (Thermospray): M/Z (MH$^+$) 328.3; $C_{21}H_{33}N_3$+H requires 328.5.

Example 22

Trans-(±)-2-(Difluoromethyl)-5-(1-benzyl-3,4-dimethyl-4-piperidinyl)-1H-benzimidazole A solution of trans-(±)-4-(1-benzyl-3,4-dimethyl-4-piperidinyl)-1,2-benzenediamine (Preparation 16, 2.00 g, 6.46 mmol) in difluoroacetic acid was refluxed for 4 hours. The reaction mixture was cooled and diluted with water (50 mL) and ethyl acetate (50 mL). The mixture was treated with 2 N sodium hydroxide solution and shaken until the aqueous layer was basic. The organic layer was separated and the aqueous layer was extracted with ethyl acetate (3×75 mL). The combined organics were washed once with saturated brine (100 mL) and dried ($Na_2SO_4$). The solvent was concentrated in vacuo to give a brown gum (2.8 g). The residue was chromatographed on Merck 230–400 mesh silica gel (75 g) eluting with ethyl acetate:hexane (50:50). The product was collected as a yellow syrup which solidified under vacuum (2.3 g).

NMR $\delta_H$(300 MHz, $CDCl_3$) (selected data from free base): 0.75 (3H, d), 1.35 (3H, s), 3.45 (1H, d), 3.65 (1H, d), 6.85 (1H, t), 7.20–7.40 (7H, m), 7.75 (1H, m) and 9.85–10.05 (1H, br s). MS (Electrospray): M/Z (MH$^+$) 370.0; $C_{22}H_{25}F_2N_3$+H requires 370.2.

Example 23

Trans-(±)-2-(Difluoromethyl)-5-(1-pentyl-3,4-dimethyl-4-piperidinyl)-1H-benzimidazole A solution of trans-(±)-2-(difluoromethyl)-5-(3,4-dimethyl-4-piperidinyl)-1H-benzimidazole (Preparation 17, 50 mg, 0.18 mmol) in methanol (4 mL) was cooled to 0° C. and treated with valeraldehyde (16 mg, 20 μL, 0.18 mmol) and sodium triacetoxyborohydride (53 mg, 0.25 mmol). The solution was left to warm to room temperature and stirred for 16 hours. The reaction mixture was concentrated in vacuo and the residue was partitioned between ethyl acetate (75 mL) and saturated sodium bicarbonate solution (75 mL). The organic layer was separated and the aqueous layer was extracted with ethyl acetate (3×50 mL). The combined organics were dried ($Na_2SO_4$) and then concentrated in vacuo to give a clear gum. The residue was purified on a silica (5 g) Sep-Pak™ eluting with ethyl acetate:hexane (20:80) to give the title compound as a clear glass (29 mg).

NMR $\delta_H$(300 MHz, $CDCl_3$) (selected data from free base): 0.70 (3H, d), 0.90 (3H, t), 1.35 (3H, s), 2.55–2.70 (2H, m), 2.95 (1H, m), 6.85 (1H, t), 7.35 (1H, d) and 7.45–7.65 (2H, m). MS (Electrospray): M/Z (MH$^+$) 350.1; $C_{20}H_{29}F_2N_3$+H requires 350.2.

Example 24

Trans-(±)-2-(Difluoromethyl)-5-[1-(2-benzyloxyethyl)-3,4-dimethyl-4-piperidinyl]-1H-benzimidazole A solution of trans-(±)-2-(difluoromethyl)-5-(3,4-dimethyl-4-piperidinyl)-1H-benzimidazole (Preparation 17, 50 mg, 0.18 mmol) in methanol (4 mL) was cooled to 0° C. and treated with benzyloxyacetaldehyde (27 mg, 0.18 mmol) and sodium triacetoxyborohydride (53 mg, 0.25 mmol). The solution was left to warm to room temperature and stirred for 16 hours. The reaction mixture was concentrated in vacuo and the residue was partitioned between ethyl acetate (75 mL) and saturated sodium bicarbonate solution (75 mL). The organic layer was separated and the aqueous layer was extracted with ethyl acetate (3×50 mL). The combined organics were dried ($Na_2SO_4$) and then concentrated in vacuo to give a clear gum. The residue was purified on a silica (5 g) Sep-Pak™ eluting with ethyl acetate:hexane (20:80) to give an off-white solid (32 mg).

NMR $\delta_H$(300 MHz, $CDCl_3$) (selected data from free base): 0.70 (3H, d), 1.35 (3H, s), 3.65 (2H, t), 4.55 (2H, s), 6.90 (1H, t), 7.20–7.35 (5H, m) and 7.40–7.75 (3H, m). MS (Electrospray): M/Z (MH$^+$) 414.1; $C_{24}H_{29}F_2N_3O$+H requires 414.2.

Example 25

Trans-(±)-2-(Difluoromethyl)-5-[1-(2-phenoxyethyl)-3,4-dimethyl-4-piperidinyl]-1H-benzimidazole A solution of trans-(±)-2-(difluoromethyl)-5-(3,4-dimethyl-4-piperidinyl)-1H-benzimidazole (Preparation 17, 50 mg, 0.18 mmol) in methanol (4 mL) was cooled to 0° C. and treated with 2-phenoxyacetaldehyde (25 mg, 0.18 mmol) and sodium triacetoxyborohydride (53 mg, 0.25 mmol). The solution was left to warm to room temperature and stirred for 16 hours. The reaction mixture was concentrated in vacuo and the residue was partitioned between ethyl acetate (75 mL) and saturated sodium bicarbonate solution (75 mL). The organic layer was separated and the aqueous layer was extracted with ethyl acetate (3×50 mL). The combined organics were dried ($Na_2SO_4$) and then concentrated in vacuo to give a clear gum. The residue was purified on a silica (5 g) Sep-Pak™ eluting with ethyl acetate:hexane (20:80) to yield the title compound as a white solid (19 mg).

NMR $\delta_H$(300 MHz, $CDCl_3$) (selected data from free base): 0.75 (3H, d) 1.35 (3H, s), 4.10 (2H, t), 6.85 (1H, t), 6.80–6.95 (2H, m), 7.25–7.55 (5H, m) and 7.75 (1H, m). MS (Thermospray): M/Z (MH$^+$) 400.1; $C_{23}H_{27}F_2N_3O$+H requires 400.2.

Example 26

Trans-(±)-2-(Difluoromethyl)-5-[1-(3-phenoxypropyl)-3,4-dimethyl-4-piperidinyl]-1H-benzimidazole A solution of trans-(±)-2-(difluoromethyl)-5-(3,4dimethyl-4-piperidinyl)-1H-benzimidazole (Preparation 17, 50 mg, 0.18 mmol) in methanol (4 mL) was cooled to 0° C. and treated with 3-phenoxypropanal (27 mg, 0.18 mmol) and sodium triacetoxyborohydride (53 mg, 0.25 mmol). The solution was allowed to warm to room temperature and stirred for 16 hours. The reaction mixture was concentrated in vacuo and the residue was partitioned between ethyl acetate (75 mL) and saturated sodium bicarbonate solution (75 mL). The organic layer was separated and the aqueous layer was extracted with ethyl acetate (3×50 mL). The combined organics were dried ($Na_2SO_4$) and then concentrated in vacuo to give a clear gum. The residue was purified on a silica (5 g) Sep-Pak™ eluting with ethyl acetate:hexane (20:80) to yield the title compound as an off-white gum (20 mg).

NMR δ$_H$(300 MHz, CDCl$_3$) (selected data from free base): 0.75 (3H, d), 1.35 (3H, s), 4.05 (2H, t), 6.90 (1H, t), 6.85–6.95 (3H, m) and 7.20–7.40 (4H, m). MS (Electrospray): M/Z (MH$^+$) 414.1; C$_{24}$H$_{29}$F$_2$N$_3$O+H requires 414.2.

Example 27

Trans-(±)-2-(Difluoromethyl)-5-[1-(4-methylphenethyl)-3,4-dimethyl-4-piperidinyl]-1H-benzimidazole A solution of trans-(±)-2-(difluoromethyl)-5-(3,4-dimethyl-4-piperidinyl)-1H-benzimidazole (Preparation 17, 50 mg, 0.18 mmol) in methanol (4 mL) was cooled to 0° C. and treated with 2-(4-methylphenyl)-acetaldehyde (24 mg, 0.18 mmol) and sodium triacetoxyborohydride (53 mg, 0.25 mmol). The solution was left to warm to room temperature and stirred for 16 hours. The reaction mixture was concentrated in vacuo and the residue was partitioned between ethyl acetate (75 mL) and saturated sodium bicarbonate solution (75 mL). The organic layer was separated and the aqueous layer was extracted with ethyl acetate (3×50 mL). The combined organics were dried (Na$_2$SO$_4$) and then concentrated in vacuo to give a clear gum. The residue was purified on a silica (5 g) Sep-Pak™ eluting with ethyl acetate:hexane (20:80) to give the title compound as a light brown gum (16 mg).

NMR δ$_H$(300 MHz, CDCl$_3$) (selected data from free base): 0.75 (3H, d), 1.35 (3H, s), 2.35 (3H, s), 2.95 (1H, m), 6.90 (1H, t), 6.95–7.05 (3H, m), 7.35 (1H, m) and 7.75 (1H, m). MS (Electrospray): M/Z (MH$^+$) 398.1; C$_{24}$H$_{29}$F$_2$N$_3$+H requires 398.2.

Example 28

Trans-(±)-2-Methyl-6-(1-hexyl-3,4-dimethyl-4-piperidinyl)-1,3-benzoxazole

To a stirred solution of trans-(±)-2-amino-5-(1-hexyl-3,4-dimethyl-4-piperidinyl)phenol (Preparation 19, 194 mg, 0.637 mmol), triethylamine (98 μL, 0.701 mmol) and acetyl chloride (50 μL, 0.701 mmol) in xylenes (10 mL) was added pyridinium p-toluenesulfonate (80 mg, 0.319 mmol) and the reaction mixture was heated to reflux overnight. Upon cooling, the reaction mixture was diluted with water (100 mL) and extracted with ethyl acetate (3×100 mL). The combined extracts were dried (Na$_2$SO$_4$) filtered and concentrated in vacuo to give the crude product which was purified via silica gel chromatography eluting with a gradient of ethyl acetate:dichloromethane:ammonium hydroxide (150:349:1 to 200:299:1) to give the title compound (117 mg) as a pale yellow oil.

NMR δ$_H$(400 MHz, C$_6$D$_6$) (selected data from free base): 0.86 (m, 6H), 1.19 (s, 3H), 1.21–1.34 (m, 7H), 1.43 (m, 2H), 1.78 (m, 1H), 2.08 (s, 3H), 2.09–2.35 (m, 4H), 2.45 (m, 2H), 2.68 (m, 1H), 7.06 (dd, 1H), 7.28 (d, 1H) and 7.61 (d, 1H). MS (APCI$^+$): M/Z (MH$^+$) 329.3; C$_{21}$H$_{32}$N$_2$O+H requires 329.3.

Example 29

Trans-(±)-6(1-Hexyl-3,4-dimethyl-4-piperidinyl)-1,3-benzoxazole

To a stirred solution of trans-(±)-2-amino-5-(1-hexyl-3,4-dimethyl-4-piperidinyl)phenol (Preparation 19, 109 mg, 0.358 mmol), triethylamine (55 μL, 0.394 mmol) and triethyl orthoformate (66 μL, 0.394 mmol) in xylenes (10 mL) was added pyridinium p-toluenesulfonate (5 mg, 2 μmol) and the reaction mixture was heated to reflux overnight. Upon cooling, the reaction mixture was diluted with water (100 mL) and extracted with ethyl acetate (3×100 mL). The combined extracts were dried (Na$_2$SO$_4$), filtered and concentrated in vacuo to give the crude product which was purified via silica gel chromatography eluting with ammonium hydroxide:methanol:dichloromethane (1:10:489) to give the title compound (76 mg) as a pale yellow oil.

NMR δ$_H$(400 MHz, C$_6$D$_6$) (selected data from free base): 0.79 (d, 3H), 0.86 (t, 3H), 1.15 (s, 3H), 1.23–1.33 (m, 7H), 1.46 (m, 2H), 1.75 (m, 1H), 2.06–2.31 (m, 4H), 2.39 (m, 2H), 2.66 (m, 1H), 7.02 (dd, 1H), 7.29 (m, 2H) and 7.66 (d, 1H). MS (APCI$^+$): M/Z (MH$^+$) 315.3; C$_{20}$H$_{30}$N$_2$O+H requires 315.2.

Example 30

Trans-(±)-2-Ethyl-6-(1-hexyl-3,4-dimethyl-4-piperidinyl)-1,3-benzoxazole

To a stirred solution of trans-(±)-2-amino-5-(1-hexyl-3,4-dimethyl-4-piperidinyl)phenol (Preparation 19, 145 mg, 0.476 mmol), triethylamine (73 μL, 0.524 mmol) and propionyl chloride (46 μL, 0.524 mmol) in xylenes (10 mL) was added pyridinium p-toluenesulfonate (4 mg, 2 μmol) and the reaction mixture was heated to reflux for 120 h. Upon cooling, the reaction mixture was diluted with water (100 mL) and extracted with ethyl acetate (3×100 mL). The combined extracts were dried (Na$_2$SO$_4$), filtered and concentrated in vacuo to give the crude product which was purified via silica gel chromatography eluting with ammonium hydroxide:methanol:dichloromethane (1:10:489) to give the title compound (89 mg) as a pale yellow oil.

NMR δ$_H$(400 MHz, C$_6$D$_6$) (selected data from free base): 0.85 (m, 6H), 1.12 (t, 3H), 1.20 (s, 3H), 1.22–1.36 (m, 7H), 1.44 (m, 2H), 1.79 (m, 1H), 2.09–2.36 (m, 4H), 2.45 (m, 2H), 2.52 (q, 2H), 2.69 (m, 1H), 7.04 (dd, 1H), 7.30 (d, 1H) and 7.64 (d, 1H). MS (APCI$^+$): M/Z (MH$^+$) 343.3; C$_{21}$H$_{34}$N$_2$O+H requires 343.3.

Example 31

Trans-(±)-6-(1-Hexyl-3,4-dimethyl-4-piperidinyl)-1,3-benzoxazol-2(3H)-one

To a stirred solution of trans-(±)-2-amino-5-(1-hexyl-3,4-dimethyl-4-piperidinyl)phenol (Preparation 19, 183 mg, 0.601 mmol) in N,N-dimethylformamide (3 mL) was added 1,1'-carbonyldiimidazole (107 mg, 0.661 mmol) and the reaction mixture was stirred at room temperature for 2 hours. The reaction mixture was diluted with saturated aqueous sodium bicarbonate (100 mL) and extracted with dichloromethane (3×100 mL). The combined extracts were washed with brine (100 mL), dried (Na$_2$SO$_4$), filtered and then concentrated in vacuo to give the crude product which was purified via silica gel chromatography eluting with a gradient of methanol:dichloromethane:ammonium hydroxide (10:489:1 to 15:484:1) to give the title compound (82 mg) as a pale yellow oil.

NMR δ$_H$(400 MHz, C$_6$D$_6$) (selected data from free base): 0.81 (d, 3H), 0.85 (t, 3H), 1.10 (s, 3H), 1.23–1.30 (m, 7H), 1.44 (m, 2H), 1.67 (m, 1H), 2.07–2.45 (m, 6H), 2.72 (m, 1H), 6.62 (d, 1H), 6.76 (dd, 1H), 6.90 (d, 1H) and 8.15 (br s, 1H). MS (APCI$^+$): M/Z (MH$^+$) 331.3; C$_{21}$H$_{30}$N$_2$O+H requires 331.2.

PREPARATION OF STARTING MATERIALS

Preparation 1

Trans-(±)-N-[3-(1-Hexyl-3,4-dimethyl-4-piperidinyl)-phenyl]acetamide

To a stirred solution of trans-(±)-3-(1-hexyl-3,4-dimethyl-4-piperidinyl)aniline(Preparation 23, 2.0 g, 6.93 mmol) in dichloromethane (56 mL) and triethylamine (14 mL) was added acetyl chloride (0.988 mL, 1.09 g, 13.9 mmol) dropwise. The turbid orange mixture was stirred for 60 hours at room temperature and the reaction partitioned between saturated sodium bicarbonate solution (50 mL) and dichloromethane (100 mL). The organic phase was washed with brine (50 mL) and both aqueous phases extracted with dichloromethane. The combined organics were dried (MgSO$_4$) then concentrated in vacuo. The crude residue was chromatographed on Merck 230–400 mesh silica gel (25 g) using ethyl acetate:0.5 N ammonia in dioxan (98:2) as the eluant to give the amide (2.30 g) as an orange oil.

NMR $\delta_H$(300 MHz, CDCl$_3$) (selected data): 0.80 (3H, d), 0.90 (3H, t), 2.15 (3H, s) and 7.0–7.4 (4H, m). MS (Thermospray): M/Z (MH$^+$) 331.6; $C_{21}H_{34}N_2O$+H requires 331.3.

Preparation 2

Trans-(±)-N-[2-Nitro-5-(1-hexyl-3,4-dimethyl-4-piperidinyl)phenyl]acetamide

To a solution of trans-(±)-N-[3-(1-hexyl-3,4-dimethyl-4-piperidinyl)-phenyl]acetamide (Preparation 1, 2.29 g, 6.93 mmol) in dry acetonitrile (45 mL), cooled in an ice bath, was added nitronium tetrafluoroborate (1.1 g, 7.62 mmol) portionwise. The reaction was stirred for 45 minutes and TLC (silica plate eluted with ethyl acetate) showed starting material remaining. A further portion of nitronium tetrafluoroborate (0.55 g, 3.81 mmol) was added and the reaction stirred for another 30 minutes, this process was repeated once more (two equivalents in total). The mixture was then poured into a saturated sodium bicarbonate solution (50 mL) and extracted with ethyl acetate (50 mL). The organic phase was washed with brine (50 mL) and both separated aqueous phases extracted with ethyl acetate (50 mL). The combined organics were dried (MgSO$_4$) then concentrated in vacuo. The crude residue was chromatographed on Merck 230–400 mesh silica gel (25 g) using ethyl acetate as the eluant to give the nitrophenylacetamide (1.43 g) as an orange semi-solid.

NMR $\delta_H$(300 MHz, CDCl$_3$) (selected data): 0.80 (3H, d), 0.90 (3H, t), 1.30 (3H, s), 2.30 (3H, s), 7.1 (1H, d), 8.15 (1H, d), 8.80 (1H, s) and 10.4 (1H, br s). MS (Thermospray): M/Z (MH$^+$) 376.9; $C_{21}H_{33}N_3O_3$+H requires 376.6.

Preparation 3

Trans-(±)-N-[2-Amino-5-(1-hexyl-3,4-dimethyl-4-piperidinyl)phenyl]acetamide

A solution of trans-(±)-N-[2-nitro-5-(1-hexyl-3,4-dimethyl-4-piperidinyl)-phenyl]acetamide (Preparation 2, 1.43 g, 3.81 mmol) and 10% palladium on carbon (175 mg) in methanol (34 mL) was subjected to hydrogenation in a bomb at 415 kPa and room temperature for 48 hours. The mixture was filtered and the filtrate concentrated in vacuo to give the crude acetamide (1.4 g) as a yellow semi-solid.

NMR $\delta_H$(300 MHz, CDCl$_3$) (selected data): 0.80 (3H, s), 0.90 (3H, t), 2.20 (3H, s), and 6.75–7.20 (4H, m). MS (Thermospray): M/Z (MH$^+$) 345.3; $C_{21}H_{34}N_3O$+H requires 346.5.

Preparation 4

Trans-(±)-2-Nitro-5-(1-hexyl-3,4-dimethyl-4-piperidinyl)aniline

A solution of trans-(±)-N-[2-nitro-5-(1-hexyl-3,4-dimethyl-4-piperidinyl)-phenyl]acetamide (Preparation 2, 1.81 g, 4.82 mmol) in Claisens alkali (5 mL) (17.6 g of KOH in 12.6 mL of water made up to 50 mL with methanol) was warmed to 100° C. for 15 minutes. Hot water (5 mL) was added and the mixture heated for a further 15 minutes. The reaction was cooled and the methanol removed in vacuo. The reaction was partitioned between ethyl acetate (50 mL) and water (50 mL) and the separated aqueous layer extracted with ethyl acetate (50 mL). The combined organics were washed with brine (50 mL), dried (MgSO$_4$) then concentrated in vacuo to give the crude nitroaniline (1.23 g) as an orange oil.

NMR $\delta_H$(300 MHz, CDCl$_3$) (selected data): 0.80 (3H, s), 0.90 (3H, m), 6.10 (2H, br s), 6.60 (1H, s), 6.65 (1H, d) and 8.05 (1H, d). MS (Thermospray): M/Z (MH$^+$) 334.3; $C_{19}H_{30}N_3O_2$+H requires 334.5.

Preparation 5

Trans-(±)-4-(1-Hexyl-3,4-dimethyl-4-piperidinyl)-1,2-benzenediamine

A mixture of trans-(±)-2-nitro-5-(1-hexyl-3,4-dimethyl-4-piperidinyl)aniline (Preparation 4, 1.23 g, 3.69 mmol) and 10% palladium on charcoal (151 mg) in ethanol (20 mL) was subjected to hydrogenation in a bomb at 415 kPa and room temperature for 48 hours. The mixture was filtered through Celite®, washing with methanol and the filtrate concentrated in vacuo to give the diamine as a dark brown oil. This compound was very sensitive to air oxidation and was stored cold under an inert atmosphere.

NMR $\delta_H$(300 MHz, CDCl$_3$) (selected data): 0.80 (3H, d), 0.90 (3H, m) and 6.65 (3H, br s). MS (Thermospray): M/Z (MH$^+$) 304.6; $C_{19}H_{33}N_3$+H requires 304.5.

Preparation 6

Trans-(±)-2-iodo-5-(1-Hexyl-3,4-dimethyl-4-piperidinyl)-aniline

To a solution of trans-(±)-3-(1-hexyl-3,4-dimethyl-4-piperidinyl)aniline (Preparation 23, 272 mg, 0.94 mmol) in glacial acetic acid (5 mL) was added iodine (478 mg, 1.89 mmol) and the reaction stirred overnight. Saturated sodium bicarbonate solution was added until effervescence ceased and the mixture diluted with dichloromethane:methanol (100 mL, 10:1). The separated organic layer was washed with saturated sodium thiosulfate solution and then brine. The organic layer was dried (MgSO$_4$) then concentrated in vacuo. The residue was chromatographed on Merck 230–400 mesh silica gel using dichloromethane:ethanol:ammonium hydroxide (200:8:1) as the eluant to give the iodoanlline (88 mg) as a yellow oil.

NMR $\delta_H$(300 MHz, CDCl$_3$) (selected data): 0.80 (3H, s), 0.90 (3H, m), 4.00 (2H, br s), 6.45 (1H, d), 6.70 (1H, s) and 7.50 (1H, d). MS (Thermospray): M/Z (MH$^+$) 415.4; $C_{19}H_{31}IN_2$+H requires 415.4.

Preparation 7

Trans-(±)-2-[2-(Trimethylsilyl)ethynyl]-5-(1-hexyl-3,4-dimethyl-4-piperidinyl)aniline To a solution of trans-(±)-2-iodo-5-(1-hexyl-3,4-dimethyl-4-piperidinyl)aniline (Preparation 6, 271 mg, 0.656 mmol) in triethylamine (10 mL) under nitrogen at room temperature was added bis(triphenylphosphine) palladium(II) chloride (23 mg, 33 µmol) and copper(I) iodide (6.2 mg, 33 µmol). Trimethylsilylacetylene (120 µL, 84 mg, 0.84 mmol) was added and the mixture heated to 60°

C. overnight. The cooled reaction was diluted with ethyl acetate (50 mL), filtered through a bed of Celite®, and the filtrate washed with brine. The organic layer was dried (MgSO$_4$) and then concentrated in vacuo. The residue was chromatographed on Merck 230–400 mesh silica gel using dichloromethane:ethanol:ammonium hydroxide (300:8:1) as eluant to give the trimethylsilylaniline (211 mg) as an oil.

NMR $\delta_H$(300 MHz, CDCl$_3$) (selected data): 0.10 (9H, s), 0.80 (3H, s), 0.90 (3H, m), 4.20 (2H, br s), 6.60 (2H, m) and 7.20 (1H, d). MS (CI): M/Z (MH$^+$) 385.2; $C_{24}H_{40}N_2Si$+H requires 385.7.

Preparation 8

Trans-(±)-N-[3-(1-Benzyl-3,4-dimethyl-4-piperidinyl)-phenyl]acetamide

To a stirred solution of trans-(±)-3-(1-benzyl-3,4-dimethyl-4-piperidinyl)aniline (Preparation 27, 37.4 g, 0.15 mol) and triethylamine (70 mL, 0.50 mol) under nitrogen, was added dropwise acetyl chloride (17.4 mL, 0.244 mol). The reaction mixture was stirred for 12 hours at room temperature and then washed with a saturated solution of sodium bicarbonate (200 mL), which was then back-extracted with dichloromethane. The combined organics were dried (MgSO$_4$) then concentrated in vacuo to give a black oil (43 g). The crude oil was chromatographed on Merck 230–400 mesh silica gel (1 kg) using a gradient of CH$_2$Cl$_2$:ethyl acetate:ammonium hydroxide (60:38:2 to 0:98:2) to give the acetamide (22 g) as a brown foam.

NMR $\delta_H$(300 MHz, CDCl$_3$) (selected data): 0.80 (d, 3Hz), 1.30 (s, 3H), 2.15 (s, 3H), 3.50 (m, 2H) and 7.00–7.40 (m, 9H). MS (Thermospray): M/Z (MH$^+$) 337.1; $C_{22}H_{28}N_2O$+H requires 337.2.

Preparation 9

Trans-(±)-N-[2-Nitro-5-(1-benzyl-3,4-dimethyl-4-piperidinyl)phenyl]acetamide

A cooled (0° C.) solution of trans-(±)-N-[3-(1-benzyl-3,4-dimethyl-4-piperidinyl)phenyl]acetamide (Preparation 8, 3.7 g, 11 mmol) in acetonitrile (100 mL) was degassed five times by evacuation and then stirred under an atmosphere of nitrogen. Nitronium tetrafluoroborate (95%, 2.4 g, 16.6 mmol) was added portionwise and the reaction was stirred under nitrogen for 2 hours. The reaction was poured into saturated sodium bicarbonate solution (100 mL) and extracted into ethyl acetate (150 mL). The separated organic phase was dried (MgSO$_4$) then concentrated in vacuo. The residue was chromatographed on Merck 230–400 mesh silica gel (150 g) using a gradient of hexane:ethyl acetate:ammonium hydroxide (50:49:1 to 0:99:1) to give the product (2.2 g) as an oil.

NMR $\delta_H$(300 MHz, CDCl$_3$) (selected data from free base): 0.80 (d, 3H), 1.30 (s, 3H), 2.30 (s, 3H), 3.40 (d, 1H), 3.60 (d, 1H), 7.10 (d, 1H), 7.20–7.40 (m, 5H), 8.10 (m, 1H) and 8.80 (m, 1H). MS (Thermospray): M/Z (MH$^+$) 384.5; $C_{22}H_{27}N_3O_3$+H requires 382.5

Preparation 10

Trans-(±)-2-Nitro-5-(1-benzyl-3,4-dimethyl-4-piperidinyl)aniline

A mixture of Claisens alkali (5 mL) (prepared from KOH (17.6 g) dissolved in water (12.6 mL) and diluted to 50 mL with methanol) and trans-(±)-N-[2-nitro-5-(1-benzyl-3,4-dimethyl-4-piperidinyl)phenyl]-acetamide (Preparation 9, 2.20 g, 5.77 mmol) was heated on a steam bath for 30 minutes. Water (5 mL) was added and the reaction mixture was heated for a further 15 minutes. The reaction was cooled to room temperature and the methanol was removed by evaporation in vacuo. The residue was partitioned between water (15 mL) and dichloromethane (15 mL). The organic phase was then separated, dried (Na$_2$SO$_4$) and solvent removed by evaporation in vacuo. The residue was chromatographed on Merck 230–400 mesh silica gel (75 g), eluting with a gradient of hexane:ethyl acetate:ammonium hydroxide (49:50:1 to 0:99:1), followed by ethyl acetate:ethanol:ammonium hydroxide (89:10:1), to give the product (1.2 g) as an oil.

NMR $\delta_H$(300 MHz, CDCl$_3$) (selected data from free base): 0.80 (d, 3H), 1.30 (s, 3H), 3.40 (d, 1H), 3.60 (d, 1H), 6.00 (br s, 2H), 6.60 (m, 2H), 7.20–7.40 (m, 5H) and 8.00 (d, 1H). MS (Thermospray): M/Z (MH$^+$) 340.3; $C_{20}H_{25}N_3O_2$+H requires 340.4.

Preparation 11

Trans-(±)-2-(Trifluoromethyl)-5-(3,4-dimethyl-4-piperidinyl)-1H-benzimidazole

A solution of trans-(±)-2-nitro-5-(1-benzyl-3,4-dimethyl-4-piperidinyl)aniline (Preparation 10, 1.1 g, 2.24 mmol) in diethyl ether (3 mL) was treated with pyridine (0.18 mL, 2.24 mmol). The reaction was then cooled to 0° C., and trifluoroacetic acid (0.3 mL, 3.24 mmol) was added. Stirring under nitrogen was continued for 18 hours (during which time the reaction had warmed to room temperature), and the solvent then evaporated in vacuo. The residue was dissolved in ethyl acetate (20 mL) and washed with water (3×20 mL). The organic layer was dried (Na$_2$SO$_4$) and the solvent removed in vacuo to give the crude product (1.3 g) as an orange oil (MS (Thermospray): M/Z (MH$^+$) 436.7; $C_{22}H_{24}N_3F_3O_3$+H requires 435.5). This was dissolved in methanol (14 mL) and 10% palladium on carbon (Degussa E101, 168 mg) added. The reaction mixture was hydrogenated at 60° C., 415 kPa for 18 hours, after which it was filtered through a filter agent to remove the catalyst and the solvent was removed by evaporation in vacuo to give the crude product as a red-brown, glassy solid. This was used directly in the next step without further purification.

NMR $\delta_H$(300 MHz, CDCl$_3$) (selected data from free base): 0.90 (d, 3H), 1.40 (s, 3H), 1.80–2.40 (m, 5H), 3.10 (m, 2H) and 6.50–6.70 (m, 3H). MS (Thermospray):M/Z (MH$^+$) 298.3; $C_{15}H_{18}F_3N_3$+H requires 298.3.

Preparation 12

Trans-(±)-N-[3-(1-Benzyl-3,4-dimethyl-4-piperidinyl)-phenyl]formamide

Oxalyl chloride (1.48 mL, 2.16 g, 17 mmol) in dichloromethane (9 mL) was added dropwise to an ice cold solution of imidazole (1.16 g, 17 mmol), triethylamine (4.71 mL, 3.43 g, 34 mmol) and formic acid (0.65 mL, 0.78 g, 17 mmol) in dichloromethane (27 mL). The reaction was stirred at room temperature for 15 minutes, at which time a white precipitate was observed, and a solution of trans-(±)-3-(1-benzyl-3,4-dimethyl-4-piperidinyl)aniline (5.0 g, 17.0 mmol) in dichloromethane (10 mL) was added dropwise. The reaction was then stirred at room temperature overnight, filtered to remove triethylamine hydrochloride and the filtrate washed with saturated sodium bicarbonate solution (30 mL), water (20 mL) and brine (10 mL). The solvent was removed in vacuo and the crude residue (5 g) chromatographed on Merck 230–400 mesh silica gel (150 g) using a gradient of hexane:ethyl acetate:ammonium hydroxide (50:49:1 to 25:74:1) to give the formamide (2.4 g) as an oil.

NMR $\delta_H$(300 MHz, CDCl$_3$) (selected data from a mixture of rotamers): 0.79 (3H, d), 1.33 (3H, s), 3.45 (1H, d), 3.60 (1H, d), 6.90–7.50 (9H, m), 8.40 (0.5H, s) and 8.64 (0.5H, d). MS (CI): M/Z (MH$^+$) 323.2; C$_{21}$H$_{26}$N$_2$O+H requires 323.4.

Preparation 13

Trans-(±)-N-[2-Nitro-5-(1-benzyl-3,4-dimethyl-4-piperidinyl)phenyl]formamide

To a stirred solution of trans-(±)-N-[3-(1-benzyl-3,4-dimethyl-4-piperidinyl)phenyl]formamide (Preparation 12, 2.35 g, 7.3 mmol) in dry acetonitrile (45 mL) at 0° C. was added nitronium tetrafluoroborate (1.07 g, 8.03 mmol) portionwise over 5 minutes under nitrogen. After 1 hour, TLC (silica plate eluted with hexane:ethyl acetate:ammonium hydroxide, 50:49:1) showed incomplete reaction, and so a further portion of nitronium tetrafluoroborate (503 mg, 4.01 mmol) was added. After another 1 hour the reaction was poured into saturated sodium bicarbonate solution and extracted with ethyl acetate (2×50 mL). The combined extracts were washed with saturated brine (30 mL), dried (MgSO$_4$) and evaporated in vacuo. The crude product (3 g) was chromatographed on Merck 230–400 mesh silica gel (90 g) using a gradient of hexane:ethyl acetate:ammonium hydroxide (50:49:1 to 0:99:1) to give the nitrophenylformamide (1.1 g) as a brown gum.

NMR $\delta_H$(300 MHz, CDCl$_3$) (selected data from a mixture of rotamers): 0.80 (3H, d), 1.35 (3H, s), 3.45 (1H, d), 3.59 (1H, d), 7.10–7.40 (7H, m), 8.20 (1H, d), 8.60 (0.5, br s) and 8.80 (0.5H, br s). MS (CI): M/Z (MH$^+$) 368.0; C$_{21}$H$_{25}$N$_3$O$_3$+H requires 367.5.

Preparation 14

Trans-(±)-N-[2-Amino-5-(1-benzyl-3,4-dimethyl-4-piperidinyl)phenyl]formamide

To a solution of trans-(±)-N-[2-nitro-5-(1-benzyl-3,4-dimethyl-4-piperidinyl)phenyl]formamide (Preparation 13, 164 mg, 0.42 mmol) in water:ethanol (15:85, 25 mL) was added iron powder (213 mg, 3.8 mmol) together with calcium chloride (24 mg, 0.21 mmol). The reaction was refluxed for two hours and the solvent was removed by evaporation in vacuo. The residue was partitioned between dichloromethane (25 mL) and water (25 mL). The aqueous layer was extracted with dichloromethane (3×10 mL). The combined organics were dried (Na$_2$SO$_4$) and the solvent removed by evaporation in vacuo. The residue was chromatographed on Merck 230–400 mesh silica gel (10 g), using methanol:dichloromethane:ammonium hydroxide (10:89:1) as the eluant to give the aminophenylformamide (98 mg) as a pale yellow foam.

NMR $\delta_H$(300 MHz, CDCl$_3$) (selected data from free base): 0.80 (d, 3H), 1.30 (s, 3H), 3.40 (d, 1H), 3.60 (d, 1H), 6.70 (t, 1H), 6.90–7.0 (m, 2H), 7.10–7.30 (m, 3H) and 8.40 (m, 1H). MS (Thermospray): M/Z (MH$^+$) 338.6; C$_{21}$H$_{27}$N$_3$O+H requires 338.5.

Preparation 15

Trans-(±)-5-(3,4-Dimethyl-4-piperidinyl)-1H-benzimidazole

To a solution of trans-(±)-5-(1-benzyl-3,4-dimethyl-4-piperidinyl)-1H-benzimidazole (Example 19, 644 mg, 2.02 mmol) in methanol (10 mL) was added 10% palladium on carbon (Degussa E101, 113 mg) and the reaction was hydrogenated at 60° C. and 415 kPa for 40 hours. The reaction mixture was filtered through a filter agent to remove the catalyst. The solvent was removed by evaporation in vacuo and the crude product (240 mg) was used directly in the next step without further purification.

NMR $\delta_H$(300 MHz, CDCl$_3$) (selected data from free base): 0.70 (d, 3H), 1.40 (s, 3H), 7.0–7.40 (m, 3H) and 8.00 (d, 1H). MS (Thermospray): M/Z (MH$^+$) 230.1; C$_{14}$H$_{19}$N$_3$+H requires 230.3.

Preparation 16

Trans-(±)-4-(1-Benzyl-3,4-dimethyl-4-piperidinyl)-1,2-benzenediamine

A solution of trans-(±)-2-nitro-5-(1-benzyl-3,4-dimethyl-4-piperidinyl)aniline (Preparation 10, 5.8 g, 17.1 mmol) in ethanol (300 mL) was treated with iron powder (8.6 g, 153.9 mmol), calcium chloride (950 mg, 8.55 mmol) and water (88 mL). The reaction was then refluxed for 5 hours. A further portion of iron (4.3 g) and calcium chloride (475 mg) was added, and the reaction was refluxed for a further 3 hours. The reaction was cooled and filtered through a bed of Celite®. The reaction mixture was concentrated in vacuo and the residue partitioned between dichloromethane (150 mL) and water (150 mL). The organic layer was separated and the aqueous layer was extracted with dichloromethane (3×75 mL). The combined organics were dried (Na$_2$SO$_4$) and concentrated in vacuo to give a dark foam (4.32 g).

NMR $\delta_H$(300 MHz, CDCl$_3$) (selected data from free base): 0.90 (3H, d), 1.25 (3H, s), 3.45 (1H, d), 3.60 (11H, d), 6.55–6.70 (31H, m) and 7.15–7.25 (5H, m). MS (Electrospray): M/Z (MH$^+$) 310.1; C$_{20}$H$_{27}$N$_3$+H requires 310.2.

Preparation 17

Trans-(±)-2-(Difluoromethyl)-5-(3,4-dimethyl-4-piperidinyl)-1H-benzimidazole

A solution of trans-(±)-2-(difluoromethyl)-5-(1-benzyl-3,4-dimethyl-4-piperidinyl)-1H-benzimidazole (Example 22, 2.99 g, 5.41 mmol) in ethanol (80 mL) was treated with 10% palladium on activated charcoal (100 mg) and hydrogenated at 50° C. for 72 hours. The reaction mixture was allowed to cool and the catalyst remove by filtration through a bed of Celite®, which was washed well with ethanol. The solution was concentrated in vacuo to give a yellow foam (1.36 g).

NMR $\delta_H$(300 MHz, CDCl$_3$) (selected data from free base): 0.65 (3H, d), 1.45 (3H, s), 6.90 (1H, t), 7.35 (1H, d), 7.55 (1H, s) and 7.65 (1H, d). MS (Electrospray): M/Z (MH$^+$) 280.1; C$_{15}$H$_{19}$F$_2$N$_3$+H requires 280.2.

Preparation 18

Trans-(±)-2-Nitro-5-(1-hexyl-3,4-dimethyl-4-piperidinyl)phenol

To a stirred solution of trans-(±)-3-(1-hexyl-3,4-dimethyl-4-piperidinyl)phenol (Preparation 20, 2.88 g, 9.96 mmol) in acetonitrile (85 mL) at 0° C. was added a solution of nitronium tetrafluoroborate (1.59 g, 12.0 mmol) in acetonitrile (15 mL). After 2 hours the reaction mixture was diluted with aqueous saturated sodium bicarbonate (100 mL) and extracted with ethyl acetate (3×100 mL). The combined extracts were washed with brine (100 mL), dried (Na$_2$SO$_4$), filtered and concentrated in vacuo to give the crude product which was purified via silica gel chromatography eluting with methanol:dichloromethane:ammonium hydroxide (10:489:1) to give the title compound (1.07 g) as a yellow oil.

NMR $\delta_H$(400 MHz, $C_6D_6$) (selected data from free base): 0.71 (d, 3H), 0.87 (t, 3H), 0.92 (s, 3 H), 1.02 (m, 1H), 1.23–1.32 (m, 6H), 1.42 (m, 2H), 1.52 (m, 1H), 1.93 (m, 2H), 2.18 (m, 3H), 2.33 (m, 1H), 2.55 (m, 1H), 6.28 (dd, 1H), 6.78 (d, 1H) and 7.62 (d, 1H). MS (APCI$^+$): M/Z (MH$^+$) 335.3; $C_{19}H_{30}N_2O_3$+H requires 335.2.

Preparation 19

Trans-(±)-2-Amino-5-(1-hexyl-3,4-dimethyl-4-piperidinyl)phenol

To a solution of trans-(±)-2-nitro-5-(1-hexyl-3,4-dimethyl-4-piperidinyl)phenol (Preparation 18, 644 mg, 1.93 mmol) in tetrahydrofuran (15 mL) was added platinum (IV) oxide (9 mg, 39 mmol) and the reaction mixture was shaken under 345 kPa of hydrogen gas for 10 hours. The reaction mixture was purged with nitrogen, filtered under nitrogen and the crude product was then (typically) employed directly in the subsequent reaction. On some occasions, the product was purified after concentration in vacuo via silica gel chromatography eluting with methanol:dichloromethane:ammonium hydroxide (10:989:1) to give the title compound as an air-sensitive oil.

NMR $\delta_H$($C_6D_6$) (selected data): 0.86 (t, 3H), 0.97 (d, 3H), 1.24–1.32 (m, 9H), 1.45 (m, 3H), 1.81 (m, 1H), 2.16–2.41 (m, 5H), 2.53 (m, 1H), 2.78 (m, 1H), 6.42–6.46 (m, 2H) and 6.64 (dd, 1H). MS (APCI$^+$): M/Z (MH$^+$) 305.3; $C_{19}H_{32}N_2O$+H requires 305.3.

Preparation 20

Trans-(±)-3-(1-Hexyl-3,4-dimethyl-4-piperidinyl)phenol

To a stirred solution of trans-(±)-3-(3,4-dimethyl-4-piperidinyl)phenol (J. A. Werner et al, *J. Org. Chem.*, 1996, 61, 587; 2.0 g, 9.8 mmol) in N,N-dimethylformamide (50 mL) was added sodium bicarbonate (1.76 g, 20.95 mmol) and bromohexane (1.64 g, 9.9 mmol). The reaction mixture was heated under reflux for 3 hours and then cooled to room temperature. The reaction mixture was diluted with water (100 mL) and extracted with dichloromethane (4×50 mL). The combined extracts were washed with brine (100 mL), dried (MgSO$_4$), filtered and concentrated in vacuo to give the crude product. This was purified by silica (50 g) column chromatography eluting with ethyl acetate:hexane:0.880 ammonia (30:70:1) to give the title compound as a light brown oil (2.68 g).

NMR $\delta_H$(300 MHz, CDCl$_3$) (selected data from free base): 0.75 (d, 3H), 0.85 (t, 3H), 1.15–1.25 (m, 6H), 1.3 (s, 3H), 2.0 (m, 1H), 2.35 (m, 4H), 2.6 (m, 2H) and 6.55–7.2 (m, 4H). MS (Thermospray): M/Z (MH$^+$) 290.2; $C_{19}H_{31}$NO+H requires 290.3.

Preparation 21

Trans-(±)-2-Methyl-2-[3-(1-hexyl-3,4-dimethyl-4-piperidinyl)phenoxy]propionamide To a solution of trans-(±)-3-(1-hexyl-3,4-dimethyl-4-piperidinyl)phenol (Preparation 20, 20 g, 69.2 mmol) in 1,4-dioxan (250 mL) under an atmosphere of nitrogen was added caesium carbonate (32.5 g, 100 mmol) carefully followed by sodium hydride (60% dispersion in mineral oil, 4 g, 100 mmol) in four portions over 30 min. The resultant mixture was stirred for 30 min then 2-bromo-2-methylpropionamide (16.6 g, 100 mmol) was added and the mixture was heated under reflux overnight. The reaction mixture was cooled, filtered and concentrated in vacuo to give the crude product which was purified by silica (600 g) column chromatography, eluting with a gradient of ethyl acetate:hexane:0.880 ammonia (30:70:1 to 50:50:1), to give recovered starting phenol (5.9 g) followed by the title compound as a white solid (14.3 g).

NMR $\delta_H$(300 MHz, CDCl$_3$) (selected data from free base): 0.75 (d, 3H), 0.85 (m, 3H), 2.0 (m, 1H), 2.3 (m, 4H), 2.5 (m, 2H), 2.8 (m, 1H), 5.45 (br s, 1H), 6.65 (br s, 1H) and 6.75–7.2 (m, 4H). MS (Thermospray): M/Z (MH$^+$) 375.4; $C_{23}H_{38}N_2O_2$+H requires 375.3.

Preparation 22

Trans-(±)-N-[3-(1-Hexyl-3,4-dimethyl-4-piperidinyl)-phenyl]-2-hydroxy-2-methylpropionamide To a solution of trans-(±)-2-methyl-2-[3-(1-hexyl-3,4-dimethyl-4-piperidinyl)phenoxy]propionamide (Preparation 21, 13.13 g, 35 mmol) in N-methylpyrrolidinone (175 mL) under an atmosphere of nitrogen was added sodium hydride (60% dispersion in mineral oil, 4 g, 100 mmol) in four portions over 30 min. The resultant mixture was stirred for 30 min and then heated at 170° C. overnight. The reaction mixture was cooled, carefully poured onto water (200 mL) and extracted with diethyl ether (3×150 mL). The combined extracts were washed with water (2×100 mL), dried (Na$_2$SO$_4$) and concentrated in vacuo to afford the title compound as an orange oil (12.9 g) which was used without further purification.

NMR $\delta_H$(300 MHz, CDCl$_3$) (selected data from free base): 0.8 (d, 3H), 0.9 (m, 3H), 2.0 (m, 1H), 2.3 (m, 4H), 2.5 (m, 2H), 2.8 (m, 1H), 7.05–7.55 (m, 4H) and 8.75 (br s, 1H). MS (Thermospray): M/Z (MH$^+$) 375.4; $C_{23}H_{38}N_2O_2$+H requires 375.3.

Preparation 23

Trans-(±)-3-(1-Hexyl-3,4-dimethyl-4-piperidinyl)-aniline

A solution of trans-(±)-N-[3-(1-hexyl-3,4imethyl-4-piperidinyl)phenyl]-2-hydroxy-2-methylpropionamide (Preparation 22, 12.9 g, 34.3 mmol) in 1,4-dioxan:5 N HCl (1:1, 150 mL) was heated under reflux overnight. The reaction mixture was cooled, diluted with water (100 mL) and extracted with diethyl ether (3×200 mL). The pH of the aqueous layer was adjusted to 8–9 using 5 N NaOH and extracted with dichloromethane (5×200 mL). The combined extracts were washed with brine (100 mL), dried (Na$_2$SO$_4$) and concentrated in vacuo to give the crude product which was purified by silica (200 g) column chromatography, eluting with ethyl acetate:hexane:0.880 ammonia (40:60:1), to afford the title compound as a clear oil (8.8 g).

NMR $\delta_H$(300 MHz, CDCl$_3$) (selected data from free base): 0.8 (d, 3H), 0.9 (m, 3H), 1.95 (m, 1H), 2.35 (m, 4H), 2.55 (m, 2H), 2.8 (m, 1H), 3.6 (s, 2H) and 6.5–7.1 (m, 4H). MS (Thermospray): M/Z (MH$^+$) 289.5; $C_{19}H_{32}N_2$+H requires 289.3.

Preparation 24

Trans-(±)-3-(1-Benzyl-3,4-dimethyl-4-piperidinyl)phenol

To a stirred solution of trans-(±)-3-(3,4-dimethyl-4-piperidinyl)phenol (J. A. Werner et al, *J. Org. Chem.*, 1996, 61, 587; 2.08 g, 10.15 mmol) in N,N-dimethylformamide (50 mL) was added sodium bicarbonate (1.70 g, 20.3 mmol) and benzyl bromide (1.35 mL, 11.2 mmol). The reaction mixture was heated under reflux for 90 min. The reaction mixture was then diluted with water (75 mL) and extracted with dichloromethane (100, 50 and then 25 mL). The organic fractions were dried ($Na_2SO_4$), filtered and concentrated in vacuo to give the crude product. This was purified by silica (70 g) column chromatography, eluting with ethyl acetate:hexane:0.880 ammonia (30:70:1) to give the title compound as a pale pink oil (2.66 g).

NMR $\delta_H$(300 MHz, $CDCl_3$) (selected data from free base): 0.8 (d, 3H), 1.2 (s, 3H), 2.9 (d, 1H), 3.5 (d, 1H), 3.6 (d, 1H), 6.6–6.9 (m, 3H), 7.1–7.4 (m, 6H). MS (Thermospray): M/Z ($MH^+$) 296.4; $C_{20}H_{25}NO+H$ requires 296.2.

Preparation 25

Trans-(±)-2-Methyl-2-[3-(1-benzyl-3,4-dimethyl-4-piperidinyl)phenoxy]propionamide To a solution of trans-(±)-3-(1-benzyl-3,4-dimethyl-4-piperidinyl)phenol (Preparation 24, 12.57 g, 42.6 mmol) in 1,4-dioxan (250 mL) under an atmosphere of nitrogen was added caesium carbonate (49.5 g, 152 mmol) carefully followed by anhydrous sodium hydride (4 g, 168 mmol) in four portions over 30 min. The resultant mixture was stirred for 1 hour then 2-bromo-2-methylpropionamide (20.5 g, 124 mmol) was added and the mixture was heated under reflux overnight, The reaction mixture was cooled, filtered and concentrated in vacuo to give the crude product which was purified by silica (600 g) column chromatography, eluting with a gradient of ethyl acetate:hexane:0.880 ammonia (25:75:1 to 100:0:1) to give recovered starting phenol (1.44 g), followed by the title compound as a clear oil (12.8 g).

NMR $\delta_H$(300 MHz, $CDCl_3$) (selected data from free base): 0.8 (d, 3H), 1.35 (s, 3H), 1.95 (m, 1H), 2.35 (m, 2H), 2.55 (m, 2H), 2.8 (m, 1H), 3.5 (m, 2H), 5.4 (br s, 1H), 6.65 (br s, 1H), 6.75–7.4 (m, 9H). MS (Thermospray): M/Z ($MH^+$) 381.2; $C_{24}H_{32}N_2O_2+H$ requires 381.2.

Preparation 26

Trans-(±)-N-[3-(1-Benzyl-3,4-dimethyl-4-piperidinyl)-phenyl]-2-hydroxy-2-methylpropionamide To a solution of trans-(±)-2-methyl-2-[3-(1-benzyl-3,4-dimethyl-4-piperidinyl)phenoxy]propionamide (Preparation 25, 12.77 g, 33.6 mmol) in N,N-dimethylformamide (330 mL) under an atmosphere of nitrogen was added anhydrous sodium hydride (1.65 g, 69 mmol) in four portions over 30 min. The resultant mixture was stirred for 1 hour and then heated under reflux overnight. The reaction mixture was cooled, carefully treated with water (200 mL) and stirred for 1 hour. It was then further diluted with water (300 mL) and extracted with diethyl ether (3×500 mL). The combined extracts were washed with water (300 mL) and brine (300 mL), dried ($Na_2SO_4$) and concentrated in vacuo to give a yellow foam (14.25 g) which was purified by silica (500 g) column chromatography eluting with a gradient of ethyl acetate:hexane:0.880 ammonia (25:75:1 to 30:70:1 to 40:60:1) to give the title compound as a cream solid (10.16 g).

NMR $\delta_H$(300 MHz, $CDCl_3$) (selected data from free base): 0.8 (d, 3H), 1.35 (s, 3H), 1.55 (m, 6H), 2.0 (m, 1H), 2.1–2.9 (m, 6H), 3.4–3.65 (m, 2H), 7.0–7.55 (m, 9H), 8.65 (br s, 1H). MS (Thermospray): M/Z ($MH^+$) 381.2; $C_{24}H_{32}N_2O_2+H$ requires 381.2.

Preparation 27

Trans-(±)-3-(1-Benzyl-3,4-dimethyl-4-piperidinyl)-aniline

A solution of trans-(±)-N-[3-(1-benzyl-3,4-dimethyl-4-piperidinyl)-phenyl]-2-hydroxy-2-methylpropionamide (Preparation 26, 10.1 g, 26.5 mmol) in 1,4-dioxan:5 N hydrochloric acid (1:1, 200 mL) was heated under reflux overnight. The reaction mixture was cooled and basified to pH 13 with 10 N sodium hydroxide solution. It was then diluted with water (300 mL) and extracted with diethyl ether (3×300 mL). The combined extracts were washed with water (300 ML) and brine (300 mL), dried ($Na_2SO_4$) and concentrated in vacuo to give a brown oil which was purified by silica (400 g) column chromatography, eluting with ethyl acetate:hexane:ammonium hydroxide (25:75:1) to give the title compound as a golden oil (7.6 g).

NMR $\delta_H$(300 MHz, $CDCl_3$) (selected data from free base): 0.8 (d, 3H), 1.3 (s, 3H), 1.55 (m, 1H), 1.95 (m, 1H), 2.25–2.6 (m, 4H), 2.85 (m, 1H), 3.4–3.7 (m, 2H), 6.45–7.4 (m, 9H). MS (Thermospray): M/Z ($MH^+$) 295.3; $C_{20}H_{26}N_2+H$ requires 295.2.

Biological Activity

The Ki values of certain compounds of the present invention in the opioid receptor binding assays were determined, and the compounds of Examples 3, 7, 12, 18, 21 and 28 were all found to have Ki values of 4000 nM or less for the μ receptor. The compounds of the invention also possess affinity at the δ and κ opioid receptors.

What is claimed is:

1. A compound of formula I,

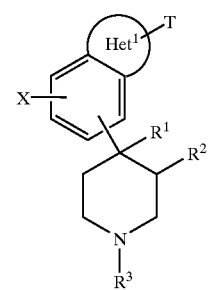

I wherein $Het^1$ represents an imidazole group;

T represents one or more optional substituents selected from H, halo, OH, =O, $C_{1-6}$ alkyl, $C_{1-6}$ alkoxy, $C_{3-6}$ cycloalkyl (which latter three groups are optionally substituted by one or more halo atoms), aryl($C_{1-6}$)alkyl (the aryl part of which is optionally substituted by one or more substituents selected from halo, $C_{1-4}$ alkyl and $C_{1-4}$ alkoxy (which latter two groups are optionally substituted by one or more halo atoms)), —N($R^{4a}$)($R^5$), —N($R^{4b}$)S(O)$_m R^6$, —N($R^{4c}$)C(O)$R^{7a}$ and —N($R^{4d}$)C(O)O$R^{7b}$, provided that when $Het^1$ contains less than three C-atoms (i.e. where the only two C-atoms are those provided by the fused benzene ring) and at least one heteroatom selected from oxygen and sulfur, then T does not represent halo or $C_{1-6}$ alkoxy (which latter group is optionally substituted by one or more halo atoms); $R^{4a}$ to $R^{4d}$ and $R^5$ independently represent H, $C_{1-6}$ alkyl (which latter group is optionally substituted by one or more halo atoms), or $R^{4a}$ and $R^5$, together with the nitrogen atom to which they are attached, form a 4- to 6-membered heterocyclic ring (which ring is optionally substituted by one or more substituents selected from $C_{1-4}$ alkyl, $C_{1-4}$ alkoxy, OH, =O, nitro, amino or halo);

$R^6$ represents $C_{1-6}$ alkyl or aryl, which two groups are optionally substituted by one or more substituents selected from halo, $C_{1-4}$ alkyl or nitro;

$R^{7a}$ and $R^{7b}$ independently represent $C_{1-6}$ alkyl, $C_{1-6}$ alkoxy, $C^{3-6}$ cycloalkyl, aryl (which four groups are optionally substituted by one or more substituents selected from halo, $C_{1-4}$ alkyl or nitro), or $R^{7a}$ represents H;

m is 0, 1 or 2;

$R^1$ and $R^2$ are each independently H or $C_{1-4}$ alkyl;

$R^3$ represents $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{8c}$, $S(O)_n R^{8d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{9a})S(O)_2 R^{10}$, $Het^2$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or —W—$A^1$—$N(R^{9b})(R^{9c})$;

n is 0, 1 or 2;

W represents a single bond, C(O) or $S(O)_p$;

$A^1$ represents a single bond or $C_{1-10}$ alkylene; provided that when both W and $A^1$ represent single bonds, then the group —$N(R^{9b})(R^{9c})$ is not directly attached to an unsaturated carbon atom;

p is 0, 1 or 2;

$R^{8a}$ to $R^{8d}$ each independently represent H, $C_{1-10}$ alky, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^3$;

provided that $R^{8d}$ does not represent H when n represents 1 or 2;

$R^{9a}$ to $R^{9c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^4$, or $R^{9b}$ and $R^{9c}$ together represent unbranched $C_{2-6}$ alkylene which alkylene group is optionally interrupted by O, S and/or an $N(R^{11})$ group and is optionally substituted by one or more $C_{1-4}$ alkyl groups;

$R^{10}$ represents $C_{1-4}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;

$R^{11}$ represents H, $C_{1-6}$ alkyl, $C_{3-8}$ cycloalkyl, $A^2$—($C_{3-8}$ cycloalkyl) or $A^2$-aryl;

$A^2$ represents $C_{1-6}$ alkylene;

$Het^2$, $Het^3$ and $Het^4$ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

X represents one or two optional substituents on the benzene ring, which substituents are selected from halo, $C_{1-4}$ alkyl, $C_{1-4}$ alkoxy (which latter two groups are optionally substituted by one or more halo atoms);

or pharmaceutically, or veterinarily, acceptable derivatives thereof.

2. A compound as claimed in claim 1, wherein $Het^1$ is fused at the 3,4-position on the benzene ring relative to the piperidine ring.

3. A compound as claimed in claim 1, wherein $R^1$ represents $C_{1-2}$ alkyl.

4. A compound as claimed in claim 1, wherein $R^2$ represents H or $C_{1-2}$ alkyl.

5. A compound as claimed in claim 1, wherein $R^3$ represents saturated $C_{1-10}$ alkyl, optionally interrupted by oxygen and/or optionally substituted by one or more substituents selected from $OR^{8c}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{9a})S(O)_2 R^{10}$, $Het^2$, phenyl (which latter group is optionally substituted by one or more substituents selected from OH, $C_{1-4}$ alkyl, $C_{1-4}$ alkoxy, $C_{2-5}$ alkanoyl, halo, nitro, amino, CN, $CH_2CN$, $CONH_2$ and $CF_3$), and/or —W—$A^1$—$N(R^{9b})(R^{9c})$.

6. A compound as claimed in claim 1, wherein $R^{8c}$ represents H, $C_{1-6}$ alkyl, $C_{3-8}$ cycloalkyl, phenyl or $C_{1-4}$ alkylphenyl (which latter two groups are optionally substituted by one or more substituents selected from OH, $C_{1-4}$ alkyl, $C_{1-4}$ alkoxy, $C_{2-5}$ alkanoyl, halo, nitro, amino, CN, $CH_2CN$, $CONH_2$ and $CF_3$); $R^{9a}$ to $R^{9c}$ each independently represent H, $C_{1-4}$ alkyl, $C_{1-2}$ alkylphenyl or aryl (which latter two groups are optionally substituted by or one or more substituents selected from $C_{1-2}$ alkyl, $C_{1-2}$ alkoxy, OH or halo); $R^{10}$ represents $C_{1-4}$ alkyl or aryl (which two groups are optionally substituted by or one or more substituents selected from $C_{1-2}$ alkyl, $C_{1-2}$ alkoxy, nitro or halo); W represents C(O) or $S(O)_2$; and/or $A^1$ represents a single bond or $C_{1-4}$ alkylene.

7. A compound as claimed in claim 1, wherein T represents H, OH, $C_{1-6}$ alkyl (optionally substituted with one or more halo atoms), $C_{1-4}$ alkoxy, $C_{4-6}$ cycloalkyl, aryl($C_{1-3}$) alkyl, —$NH(R^5)$ or —$N(H)S(O)_2 R^6$.

8. A compound as claimed in claim 1, wherein $R^5$ represents H or $C_{1-2}$ alkyl; and/or $R^6$ represents $C_{1-2}$ alkyl.

9. A compound as claimed in claim 1, wherein $R^1$ and $R^2$ both represent methyl groups in the mutually trans configuration.

10. A compound as claimed in claim 1, wherein $R^3$ represents saturated $C_{1-7}$ alkyl, optionally substituted by one or more substituents selected from CN, halo, O—($C_{1-4}$ alkyl), O-(phenyl), O—($C_{1-4}$ alkylphenyl) and phenyl (which latter three groups are optionally substituted by one or more $C_{1-4}$ alkyl groups).

11. A compound as claimed in claim 1, wherein T represents H, $NH_2$, $C_{4-6}$ cycloalkyl or $C_{1-6}$ alkyl (which latter group is optionally substituted by one or more halo atoms).

12. A compounds as claimed in claim 1, wherein T represents H, $CH_3$, $CHF_2$, $CF_3$, ethyl, isopropyl, $C_{4-5}$ cycloalkyl or $NH_2$.

13. A compound as claimed in claim 1, wherein $R^3$ represents saturated $C_{1-7}$ alkyl, optionally substituted by one or more substituents selected from O—($C_{2-4}$ alkyl), O-(phenyl), O—($C_{1-2}$ alkylphenyl) and phenyl (which latter group is optionally substituted by one or more $C_{1-2}$ alkyl groups).

14. A pharmaceutical composition comprising a compound as defined in claim 1, in an effective amount, in admixture with a pharmaceutically, or a veterinarily, acceptable adjuvant, diluent or carrier.

15. A method of treating a disease mediated by an opiate receptor, which comprises administering a therapeutically effective amount of a compound as defined in claim 1, to a patient in need of such treatment.

* * * * *